(12) United States Patent
Kudo et al.

(10) Patent No.: US 8,444,618 B2
(45) Date of Patent: May 21, 2013

(54) ABSORBENT ARTICLE AND ABSORBENT BODY

(75) Inventors: Jun Kudo, Kagawa (JP); Hideyuki Kinoshita, Kagawa (JP); Akira Hashino, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 693 days.

(21) Appl. No.: 12/531,476

(22) PCT Filed: Jan. 25, 2008

(86) PCT No.: PCT/JP2008/051108
§ 371 (c)(1),
(2), (4) Date: Dec. 14, 2009

(87) PCT Pub. No.: WO2008/114530
PCT Pub. Date: Sep. 25, 2008

(65) Prior Publication Data
US 2010/0106125 A1    Apr. 29, 2010

(30) Foreign Application Priority Data
Mar. 16, 2007    (JP) .................................. 2007-069081

(51) Int. Cl.
*A61F 13/15*    (2006.01)
*A61F 13/20*    (2006.01)

(52) U.S. Cl.
USPC ............ 604/385.11; 604/385.16; 604/385.17; 604/385.101

(58) Field of Classification Search
USPC ............ 604/385.11, 385.16, 385.17, 385.101
See application file for complete search history.

(56) References Cited

U.S. PATENT DOCUMENTS

| | | | | | |
|---|---|---|---|---|---|
| 5,853,403 | A | * | 12/1998 | Tanzer et al. | 604/385.09 |
| 5,961,508 | A | * | 10/1999 | Mayer et al. | 604/385.03 |
| 2004/0167492 | A1 | * | 8/2004 | Mizutani et al. | 604/385.17 |
| 2006/0282059 | A1 | * | 12/2006 | Fujikawa et al. | 604/385.17 |

FOREIGN PATENT DOCUMENTS

| | | |
|---|---|---|
| CN | 1159750 | 9/1997 |
| CN | 1332623 | 1/2002 |
| CN | 1711061 | 12/2005 |
| EP | 1568341 | 8/2005 |

(Continued)

OTHER PUBLICATIONS

PCT/JP2008/051108 International Search Report, Mailed May 1, 2008.

(Continued)

*Primary Examiner* — Loan Thanh
*Assistant Examiner* — Aundria Hairell
(74) *Attorney, Agent, or Firm* — Lowe Hauptman Ham & Berner, LLP

(57) ABSTRACT

An absorbent article adapted to be worn on a body includes an absorbent article main body having a longitudinal direction, a width direction perpendicular thereto, and a thickness direction perpendicular thereto; and an absorbent body overlapping the absorbent article main body along the longitudinal direction. One end section in the longitudinal direction of the absorbent body is undetachably joined to the absorbent article main body, and another end section in the longitudinal direction of the absorbent body is detachably joined to the absorbent article main body. A section of the absorbent body on a wearer-facing side that is positioned on a body side in use and that does not oppose the absorbent article main body is easier to elongate in the width direction than a section of the absorbent body on an non-wearer-facing side that opposes the absorbent article main body.

18 Claims, 16 Drawing Sheets

FOREIGN PATENT DOCUMENTS

| | | |
|---|---|---|
| EP | 1 627 618 | 2/2006 |
| JP | 53-97540 | 8/1978 |
| JP | 10-504486 | 5/1998 |
| JP | 10-286278 A | 10/1998 |
| JP | 2002159534 | 6/2002 |
| JP | 2006-198396 | 3/2006 |
| WO | 96/05790 A1 | 2/1996 |
| WO | 9605790 | 2/1996 |

OTHER PUBLICATIONS

Australian Office Action for Application No. 2008227750 mailed May 25, 2012.
Chinese Office Action for Application No. 200880014859.0 mailed Jan. 5, 2013.

* cited by examiner

ABSORBENT ARTICLE AND ABSORBENT BODY

RELATED APPLICATIONS

The present application is based on, and claims priority from, International Application PCT/JP2008/051108 filed Jan. 25, 2008 and Japanese Application Number 2007-069081, filed Mar. 16, 2007, the disclosures of which are hereby incorporated by reference herein in their entirety.

TECHNICAL FIELD

The present invention relates to absorbent articles for absorbing fluid and absorbent bodies.

BACKGROUND ART

Conventionally, as absorbent articles that absorb predetermined fluid such as menstrual blood, absorbent articles are known in which an absorbent body that absorbs fluid is disposed along the longitudinal direction on the surface of an absorbent retainer and is partly joined thereto (refer to JP-A-2002-159534, for example). Such an absorbent article is used by positioning the absorbent body so that the longitudinal direction thereof is set along the front-and-rear direction of a human body, pulling up a rear end section of the absorbent body so as to place the absorbent body in the groove of the buttocks or the like of the human body, and thereby sandwiching the absorbent body in the groove of the buttocks or the like.

DISCLOSURE OF INVENTION

Problems to be Solved by the Invention

In a conventional absorbent article as described above, it is desirable that the length of the absorbent body in a direction intersecting the longitudinal direction, that is, the width of the absorbent body is narrow because the absorbent body is placed in the buttocks or the like in using the absorbent article. However, it is desirable that the absorbent body itself is large in size because the absorbent body is required to absorb more fluid. Moreover, there is a risk that an absorbent body with narrow width may give the user a sense of insecurity regarding the absorption capacity. Therefore, it is desired that an absorbent article including an absorbent body that has a large absorption capacity and that is easy to place in the buttocks or the like be provided.

The present invention has been contrived in view of the above conventional problems, and it is an object thereof to provide an absorbent article including an absorbent body that has a large absorption capacity and that is easy to place in the buttocks or the like, and an absorbent body.

Means for Solving the Problems

A main aspect of the present invention for solving the above-described problem is an absorbent article that is worn on a body and used, including an absorbent article main body having a longitudinal direction, a width direction perpendicular thereto, and a thickness direction perpendicular thereto; and an absorbent body included by overlapping with the absorbent article main body along the longitudinal direction, wherein one end section in the longitudinal direction of the absorbent body is undetachably joined to the absorbent article main body, and another end section in the longitudinal direction of the absorbent body is detachably joined to the absorbent article main body; and a section of the absorbent body on a non-opposing side that is positioned on a body side in use and that does not oppose the absorbent article main body is easier to elongate in the width direction than a section of the absorbent body on an opposing side that opposes the absorbent article main body.

Moreover, an absorbent body that is worn on a body and used, the absorbent body being disposed by overlapping with an absorbent article main body having a longitudinal direction, a width direction perpendicular thereto, and a thickness direction perpendicular thereto, along the longitudinal direction, wherein the absorbent body is used in a state where one end section in a longitudinal direction of the absorbent body is joined to the absorbent article main body, and another end section is separated from the absorbent article main body; and a section of the absorbent body on a non-opposing side that is positioned on a body side in use and that does not oppose the absorbent article main body is more easily elongated in the width direction than a section of the absorbent body on an opposing side that opposes the absorbent article main body.

Effects Of The Invention

According to the present invention, it is possible to provide an absorbent article including an absorbent body that has a large absorption capacity and that is easy to place in the buttocks or the like, and an absorbent body.

Figure 1:
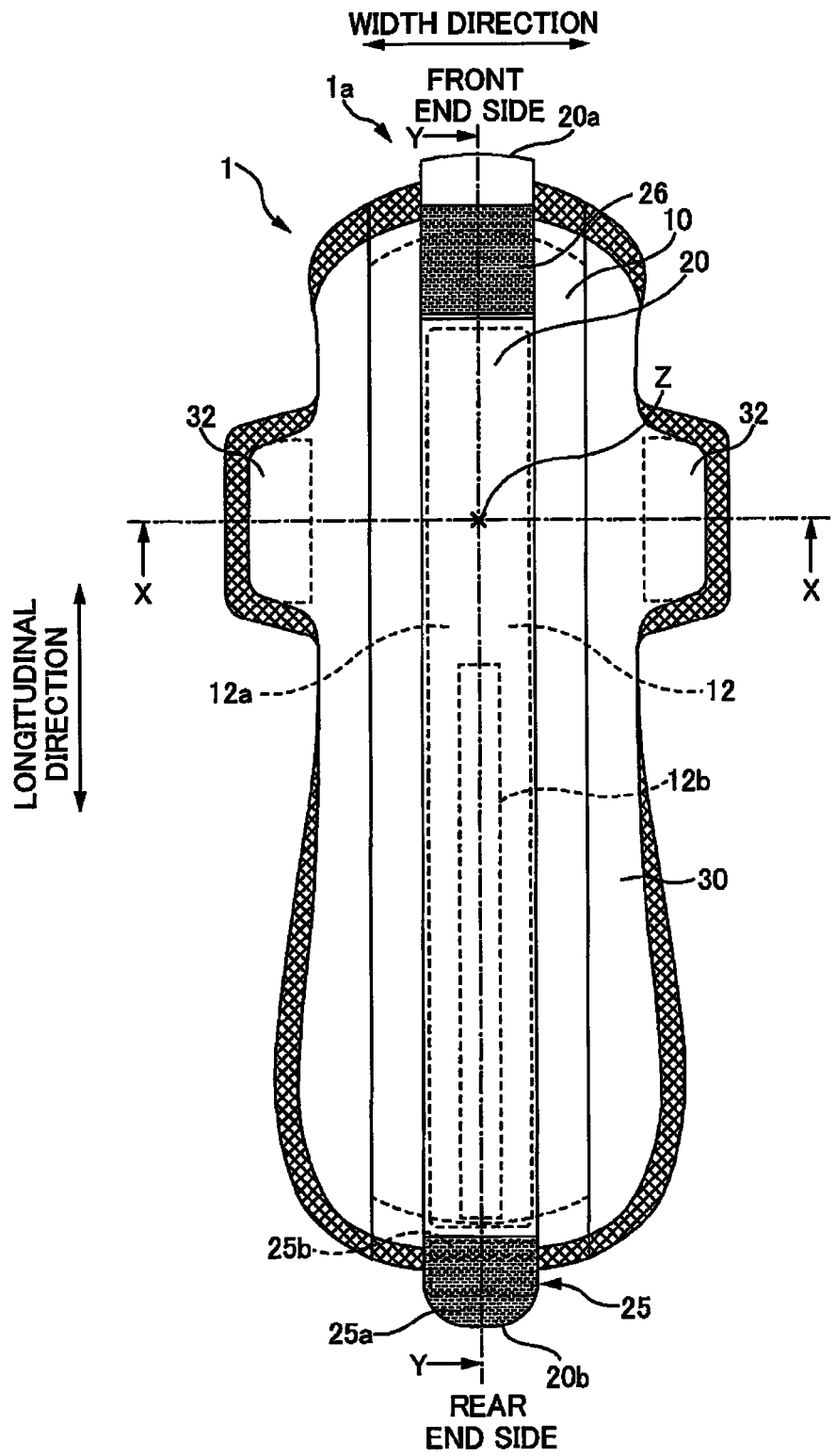
FIG. 1 is a plan view showing a surface side of an absorbent article according to the present embodiment.

LIST OF REFERENCE NUMERALS 1 absorbent article, 1a front end, 2 absorbent article, 3 buttocks, 5 absorbent article,
10 base absorbent body (absorbent article main body), 11 base absorbent body (absorbent article main body),
11a front end, 11b rear end, 12 absorbent body base material,
12a absorbent body material (absorbing member), 12b thin-walled section, 12c gathers (wrinkles),
14 surface sheet (sheet member), 15 loop member, 16 intermediate sheet,
18 leakage preventing sheet, 20 top absorbent body (absorbent body), 20a front end, 20b rear end,
21 top absorbent body (absorbent body), 21a front end, 21b rear end, 22 hook member,
23 adhesive, 25 reinforced section, 25a grasping section, 26 reinforced section, 30 back face sheet,
32 holding section, 34 release sheet, 35 adhesive, 36 wrapping sheet,
36a front end, 36b rear end, 36c edge section, 38 lead tape,
50 absorbent article, 51 top absorbent body, 52 top absorbent body,
53 top absorbent body, 60 first disk, 61 second disk, 64 third disk,
Z: position assumed to contact against the bodily discharge opening portion Best Mode For Carrying Out The Invention At least the following matters will be disclosed in the present specification and the drawings.

An absorbent article that is worn on a body and used, including: an absorbent article main body having a longitudinal direction, a width direction perpendicular thereto, and a thickness direction perpendicular thereto; and an absorbent body included by overlapping with the absorbent article main body along the longitudinal direction, wherein one end section in the longitudinal direction of the absorbent body is undetachably joined to the absorbent article main body, and another end section in the longitudinal direction of the absorbent body is detachably joined to the absorbent article main body; and a section of the absorbent body on a non-opposing side that is positioned on a body side in use and that does not oppose the absorbent article main body is easier to elongate in the width direction than a section of the absorbent body on an opposing side that opposes the absorbent article main body.

According to this absorbent article, the section of the absorbent body on the non-opposing side (the body side) that does not oppose the absorbent article main body is easier to elongate than the section of the absorbent body on the opposing side that opposes the absorbent article main body, and therefore the absorbent body can be bent to form a peak that protrudes to the non-opposing side. Thus, it is possible to increase the absorption capacity by forming an absorbent body that is wide in the width direction intersecting the longitudinal direction and to easily narrow the width of the absorbent body by bending the absorbent body so that the absorbent body forms a peak protruding to the non-opposing side. Then, at the time of using the absorbent article, the absorbent body is bent to form a peak and thus can be easily and reliably placed in the groove of the buttocks. Moreover, the absorbent body before use is maintained in a state where it is spread out substantially flat without being bent, so that the wide absorbent body is exposed and can therefore give the user a sense of security regarding the absorption capacity.

Furthermore, since one end section of the absorbent body is undetachably joined to the absorbent article main body and another end section is detachably joined thereto, the absorbent article can be supplied to the user in a state where the absorbent body is disposed in a predetermined position and opened flat without being twisted. Moreover, the other end section of the absorbent body, which is detachably joined to the absorbent article main body, can be easily detached from the absorbent article main body, and the absorbent body can be put in a state where it is joined to the absorbent article main body only at the one end section. Thus, it is possible to provide an absorbent article that can be used in a state where the side of the other end section is separated from the absorbent article main body. Accordingly, the absorbent body is more suitable for an absorbent article that is used in a state where the absorbent body is separated from the absorbent article main body and placed in the groove of the buttocks.

Furthermore, an absorbent article that is worn on a body and used including an absorbent article main body having a longitudinal direction, a width direction perpendicular thereto, and a thickness direction perpendicular thereto; and an absorbent body included by overlapping with the absorbent article main body along the longitudinal direction, wherein one end section and another end section in the longitudinal direction of the absorbent body are each detachably joined to the absorbent article main body; and a section of the absorbent body on a non-opposing side that is positioned on a body side in use and that does not oppose the absorbent article main body is easier to elongate in the width direction than a section of the absorbent body on an opposing side that opposes the absorbent article main body.

According to this absorbent article, the section of the absorbent body on the non-opposing side (the body side) that does not oppose the absorbent article main body is easier to elongate than the section of the absorbent body on the opposing side that opposes the absorbent article main body, and therefore the absorbent body can be bent to form a peak that protrudes to the non-opposing side. Thus, it is possible to increase the absorption capacity by forming an absorbent body that is wide in the width direction intersecting the longitudinal direction and to easily narrow the width of the absorbent body by bending the absorbent body so that the absorbent body forms a peak protruding to the non-opposing side. Then, at the time of using the absorbent article, the absorbent body is bent to form a peak and thus can be easily and reliably placed in the groove of the buttocks. Moreover, the absorbent body before use is maintained in a state where it is spread out substantially flat without being bent, so that the wide absorbent body is exposed and can therefore give the user a sense of security regarding the absorption capacity.

Furthermore, since one end section and another end section of the absorbent body in the longitudinal direction are each detachably joined to the absorbent article main body, the absorbent article can be supplied to the user in a state where the absorbent body is disposed in a predetermined position and opened flat without being twisted. Then, the other end section of the absorbent body, which is detachably joined to the absorbent article main body, can be easily detached from the absorbent article main body, and thus the absorbent body can be put in a state where it is joined to the absorbent article main body only at the one end section. Thus, it is possible to provide an absorbent article that can be used in a state where the side of the other end section is separated from the absorbent article main body.

Furthermore, it is possible to choose to wear the absorbent article in a state where the absorbent article main body and the absorbent body are joined to each other, or to wear the absorbent article in a state where the absorbent body is removed from the absorbent article main body as necessary. For example, in the case where a large amount of fluid is to be absorbed, the absorbent article can be used in a state where the absorbent article main body and the absorbent body are joined to each other, with the absorbent body being placed in the groove of the buttocks, and in the case where a small amount of fluid is to be absorbed, the absorbent article main body can be used alone in a state where the absorbent body is removed from the absorbent article main body. Thus, it is possible to use a single absorbent article without preparing a plurality of types of absorbent articles in order to cope with variations in the amount of fluid to be absorbed.

In the absorbent article, it is desirable that the absorbent body includes an absorbing member for absorbing fluid and a sheet member for wrapping the absorbing member, and parts of the sheet member are overlapped and adhered to each other on the opposing side.

According to this absorbent article, the opposing side that opposes the absorbent article main body has higher stiffness and lower stretchability than the non-opposing side because the parts of the sheet member wrapping the absorbing member are overlapped and adhered to each other on the opposing side. Thus, simply by wrapping the absorbing member in the sheet member, the absorbent body can have a configuration that is easily bent to form a peak protruding to the non-opposing side.

In the absorbent article, it is desirable that a thin-walled section in which a thickness of the absorbing member is made thin is included, along the longitudinal direction, in a center in the width direction of the absorbent body.

According to this absorbent article, the thin-walled section in which the thickness of the absorbing member is made thin is provided in the absorbent body along the longitudinal direction. Thus, in the case where the absorbent body is pressed by the buttocks or the like, the absorbent body can be bent at the thin-walled section along the groove of the buttocks and deformed more easily so that the width of the absorbent body is narrowed.

Furthermore, the thin-walled section is provided in the center in the width direction intersecting the longitudinal direction. Thus, the absorbent body can be bent at the center in the width direction. Since the absorbent body is bent in a balanced manner in the width direction, fluid can be absorbed more efficiently.

In the absorbent article, it is desirable that in the entire region in the longitudinal direction, the thin-walled section is biased toward the side of the other end section and included.

According to this absorbent article, the absorbent body can be deformed so that, in the entire region of the absorbent body in the longitudinal direction, the side of the other end section becomes narrower than the side of the one end section. In addition, the section of the absorbent body to be placed in the buttocks is on the side of the other end section. Thus, the absorbent body can be reliably placed in the groove of the buttocks because the thin-walled section is disposed on the side of the other end section.

In the absorbent article, it is desirable that wrinkles that will be elongated in the width direction are formed in the sheet member.

According to this absorbent article, the wrinkles that will be elongated in the width direction intersecting the longitudinal direction are formed in the sheet member, and therefore the non-opposing side of the absorbent body that does not oppose the absorbent article main body can be more easily elongated than the opposing side that opposes the absorbent article main body, and the absorbent body can be easily bent so as to protrude to the non-opposing side. Herein, a region where the wrinkles are formed, in the width direction, may be wider in the section of the sheet member on the non-opposing side than in the section on the opposing side. Also in this case, the non-opposing side can be more easily elongated than the opposing side, and the absorbent body can be easily bent so as to protrude to the non-opposing side.

In the absorbent article, it is desirable that a leakage preventing sheet for preventing fluid from leaking is included in the absorbent body, and a region where the leakage preventing sheet is included, in the width direction, is wider in the section on the opposing side than in the section on the non-opposing side.

According to this absorbent article, in the absorbent body, the region where the leakage preventing sheet is provided is wider in the section on the non-opposing side than in the section on the opposing side. Thus, the non-opposing side can be more easily elongated than the opposing side, which is difficult to expand and contract due to the leakage preventing sheet, and the absorbent body can be more easily bent so as to protrude to the non-opposing side.

In the absorbent article, it is desirable that the leakage preventing sheet is adhered together with the sheet member.

According to this absorbent article, the leakage preventing sheet, which is formed in the wider region in the section on the non-opposing side than in the region in the section on the opposing side of the absorbent body, is adhered together with the sheet member. Thus, the non-opposing side of the absorbent article can be even more easily elongated than the opposing side, and the absorbent body can have a configuration that can be easily bent so as to protrude to the non-opposing side.

In the absorbent article, it is desirable that the 5% elongation strength in the width direction of the sheet member on the non-opposing side is equal to or less than 80% of the 5% elongation strength in the width direction on the opposing side.

According to this absorbent article, the 5% elongation strength in the width direction of the sheet member on the non-opposing side is equal to or less than 80% of the 5% elongation strength in the width direction on the opposing side, and thus the absorbent body can be more easily bent to form a peak that protrudes to the non-opposing side. In the absorbent article, it is desirable that the 5% elongation strength in the width direction of the sheet member on the non-opposing side is less than 3 N/25 mm.

According to this absorbent article, since the 5% elongation strength in the width direction of the sheet member on the non-opposing side is less than 3 N/25 mm, the absorbent body can be more easily bent to form a peak that protrudes to the non-opposing side even further.

In the absorbent article, it is desirable that the absorbent article main body is formed with another absorbent body that is different from the forementioned absorbent body.

According to this absorbent article, since the absorbent body is also included to the absorbent article main body, the absorbent body becomes two-layered, and thus an absorbent article with further higher absorbency can be provided.

In the absorbent article, it is desirable that the absorbent body is deformed into a mountain-folded shape by being positioned along the bodily groove.

According to this absorbent article, the absorbent body that has been deformed into a mountain-folded shape can be easily placed in the bodily groove by being positioned therealong.

Moreover, an absorbent body that is worn on a body and used, the absorbent body being disposed by overlapping with an absorbent article main body having a longitudinal direction, a width direction perpendicular thereto, and a thickness direction perpendicular thereto, along the longitudinal direction, wherein the absorbent body is used in a state where one end section in a longitudinal direction of the absorbent body is joined to the absorbent article main body, and another end section is separated from the absorbent article main body; and a section of the absorbent body on a non-opposing side that is positioned on a body side in use and that does not oppose the absorbent article main body is more easily elongated in the width direction than a section of the absorbent body on an opposing side that opposes the absorbent article main body.

According to this absorbent body, since the section on the non-opposing side (the body side) that does not oppose the absorbent article main body is easier to elongate than the section on the opposing side that opposes the absorbent article main body, an absorbent body that can be bent to form a peak protruding to the non-opposing side can be realized. Therefore, it is possible to increase the absorption capacity of the absorbent body by forming an absorbent body that is wide in the width direction intersecting the longitudinal direction, and to easily narrow the width of the absorbent body by bending the absorbent body so that the absorbent body forms a peak protruding to the non-opposing side. And at the time of using the absorbent body, the absorbent body can be bent to form a peak and thus can be easily and reliably placed in the groove of the buttocks. Moreover, the absorbent body before use is maintained in a state where it is spread out substantially flat without being bent, so that the wide absorbent body is exposed and can therefore give the user a sense of security regarding the absorption capacity.

Furthermore, at the time of wearing the absorbent article, since it is hard for the absorbent body to be removed from the absorbent article because the one end section of the absorbent body is joined to the absorbent article main body, the absorbent body that is easily worn which overlaps with the absorbent article main body can be realized. Moreover, since the side of the other end section of the absorbent body is separated from the absorbent article main body in use, the absorbent body is more suitable as an absorbent body that is used in a state where the side of the other end section is separated from the absorbent article main body and placed in the groove of the buttocks.

In such an absorbent body, it is desirable that the absorbent body has an absorbing member for absorbing fluid and a sheet member for wrapping the absorbing member; and parts of the sheet member are overlapped and adhered to each other on the opposing side.

According to this absorbent body, the opposing side that opposes the absorbent article main body has higher stiffness and lower stretchability than the non-opposing side because the parts of the sheet member wrapping the absorbing member are overlapped and adhered to each other on the opposing side. Thus, by simply wrapping the absorbing member in the sheet member, it is possible to realize an absorbent body that can be easily bent to form a peak protruding to the non-opposing side.

In the absorbent body, it is desirable that a thin-walled section in which the thickness of the absorbing member is made thin is included in a center in the width direction along the longitudinal direction.

According to this absorbent body, since the thin-walled section in which the thickness of the absorbing member is made thin is formed along the longitudinal direction, in the case where the absorbent body is pressed by the buttocks or the like, the absorbent body can be bent at the thin-walled section along the groove of the buttocks and easily deformed so that the width of the absorbent body is narrowed even further.

Furthermore, since the absorbent body can be bent at the center in the width direction, and the absorbent body is bent in a balanced manner in the width direction, fluid can be efficiently absorbed by the absorbent body from the bent section to both sides thereof in the width direction.

In the absorbent body, it is desirable that in the entire region in the longitudinal direction, the thin-walled section is biased toward the side of the other end section and included.

According to this absorbent body, the absorbent body can be deformed so that, in the entire region of the absorbent body in the longitudinal direction, the side of the other end section becomes narrower than the side of the one end section. In addition, the section to be placed in the buttocks is on the side of the other end section. Thus, it is possible to realize an absorbent body that can be reliably placed in the groove of the buttocks because the thin-walled section is disposed on the side of the other end section.

In the absorbent body, it is desirable that wrinkles that will be elongated in the width direction are foamed in the sheet member. According to this absorbent body, since the wrinkles that will be elongated in the width direction intersecting the longitudinal direction are formed in the sheet member, the non-opposing side of the absorbent body that does not oppose the absorbent article main body can be more easily elongated than the opposing side that opposes the absorbent article main body, and the absorbent body can be easily bent so as to protrude to the non-opposing side. Herein, a region where the wrinkles are formed, in the width direction, may be wider in the section on the non-opposing side than in the section on the opposing side. Also in this case, the non-opposing side can be more easily elongated than the opposing side, and the absorbent body can be easily bent so as to protrude to the non-opposing side.

In the absorbent body, it is desirable that a leakage preventing sheet for preventing fluid from leaking is included, and a region where the leakage preventing sheet is included, in the width direction, is wider in the section on the opposing side than in the section on the non-opposing side.

According to this absorbent body, since the region where the leakage preventing sheet is formed is wider in the section on the non-opposing side than in the section on the opposing side, the non-opposing side can be more easily elongated than the opposing side, which is difficult to expand and contract due to the leakage preventing sheet, and the absorbent body can be easily bent so as to protrude to the non-opposing side. In the absorbent body, it is desirable that the leakage preventing sheet is adhered together with the sheet member.

According to this absorbent body, since the leakage preventing sheet that is formed in the wider region in the section on the non-opposing side than in the section on the opposing side is adhered together with the sheet member, the non-opposing side of the absorbent article can be even more easily elongated than the opposing side, and the absorbent body can have a configuration that can be more easily bent so as to protrude to the non-opposing side.

In the absorbent body, it is desirable that the 5% elongation strength in the width direction of the sheet member on the non-opposing side is equal to or less than 80% of the 5% elongation strength in the width direction on the opposing side.

According to this absorbent body, since the 5% elongation strength in the width direction of the sheet member on the non-opposing side is equal to or less than 80% of the 5% elongation strength in the width direction on the opposing side, the absorbent body can be more easily bent to form a peak that protrudes to the non-opposing side.

In the absorbent body, it is desirable that the 5% elongation strength in the width direction of the sheet member on the non-opposing side is less than 3 N/25 ma.

According to this absorbent body, since the 5% elongation strength in the width direction of the sheet member on the non-opposing side is less than 3 N/25 mm, the absorbent body can be more easily bent to faum a peak that protrudes to the non-opposing side even further.

In the absorbent body, it is desirable that the absorbent body is deformed into a mountain-folded shape by being positioned along the bodily groove.

According to this absorbent body, it is possible that the absorbent body is deformed into a mountain-folded shape by being positioned along the bodily groove, and is easily placed in the bodily groove.

Embodiments

First, the outline of the configuration of an absorbent article according to an embodiment of the invention will be described. The absorbent article of this embodiment is a sanitary napkin. In the following explanation, the side that is brought into contact with the body is referred to as a surface side, the side that is brought into contact with an undergarment is referred to as a back face side, the end that is positioned on the front side of the human body when worn is referred to as a front end, and the end that is positioned on the rear side is referred to as a rear end.

Figure 2:
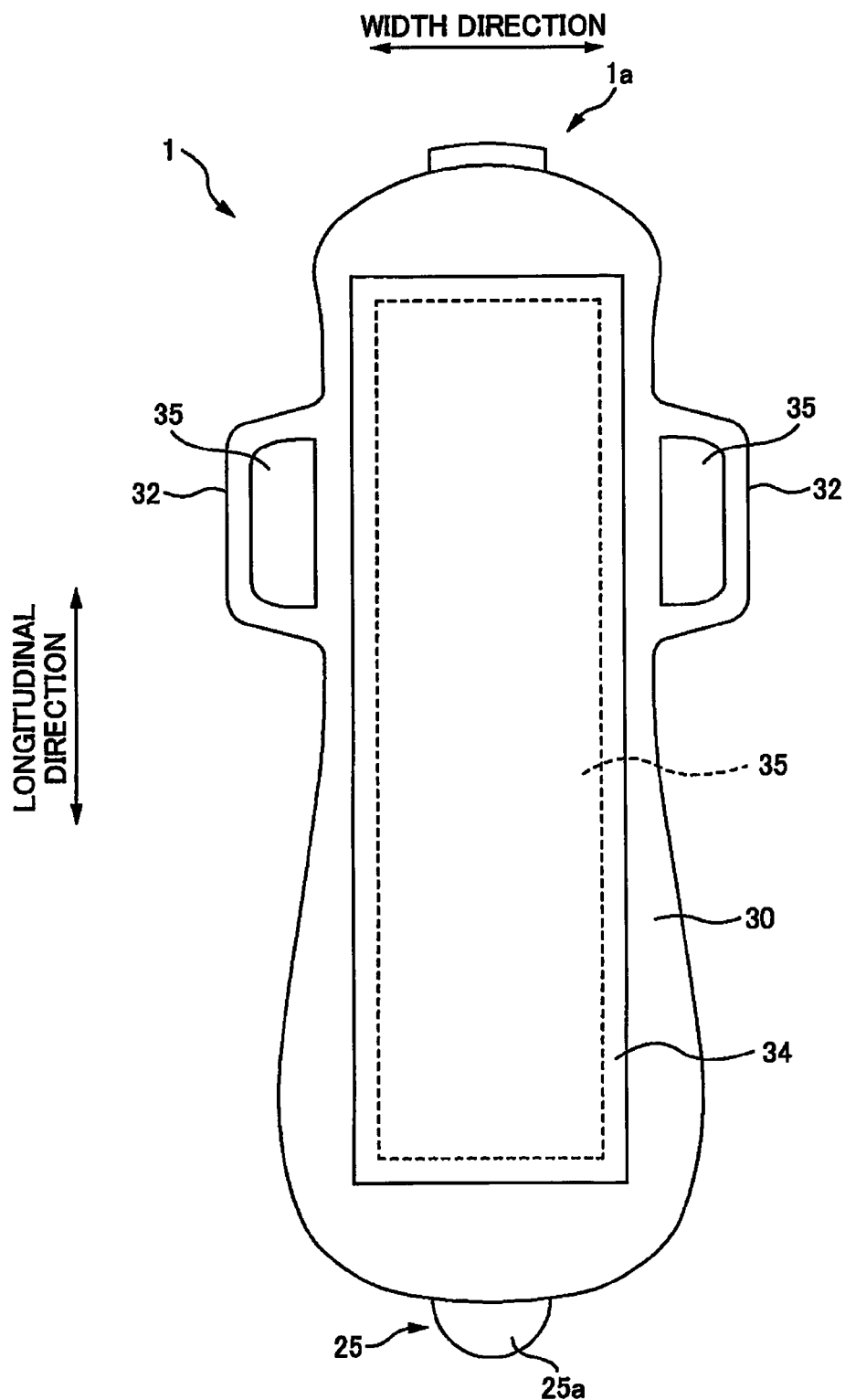
FIG. 2 is a view showing a back face side of the absorbent article according to the present embodiment.
Figure 3:
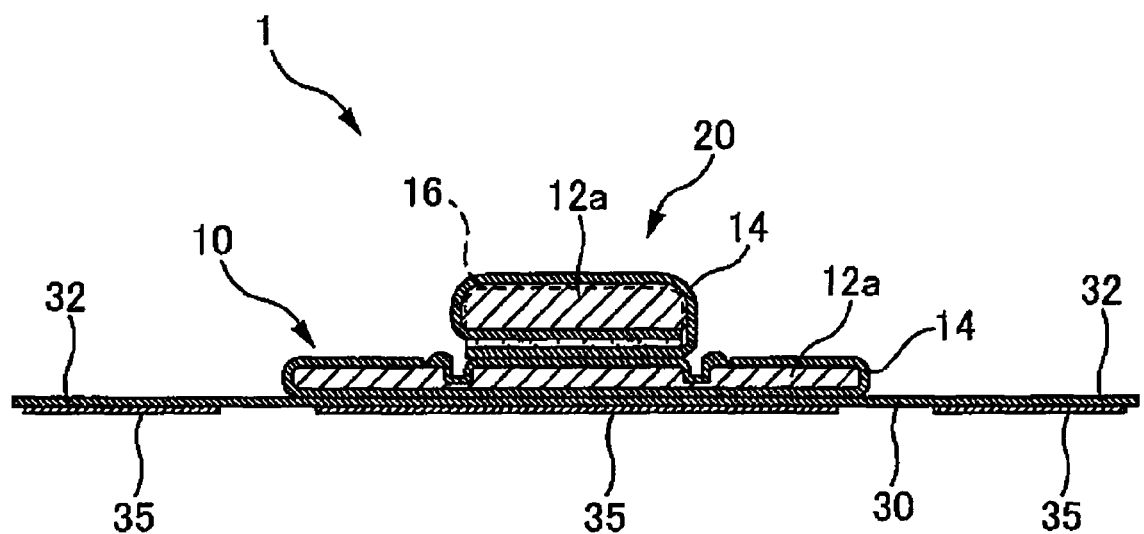
FIG. 3 is a cross-sectional view taken along line X-X in FIG. 1.
Figure 4:
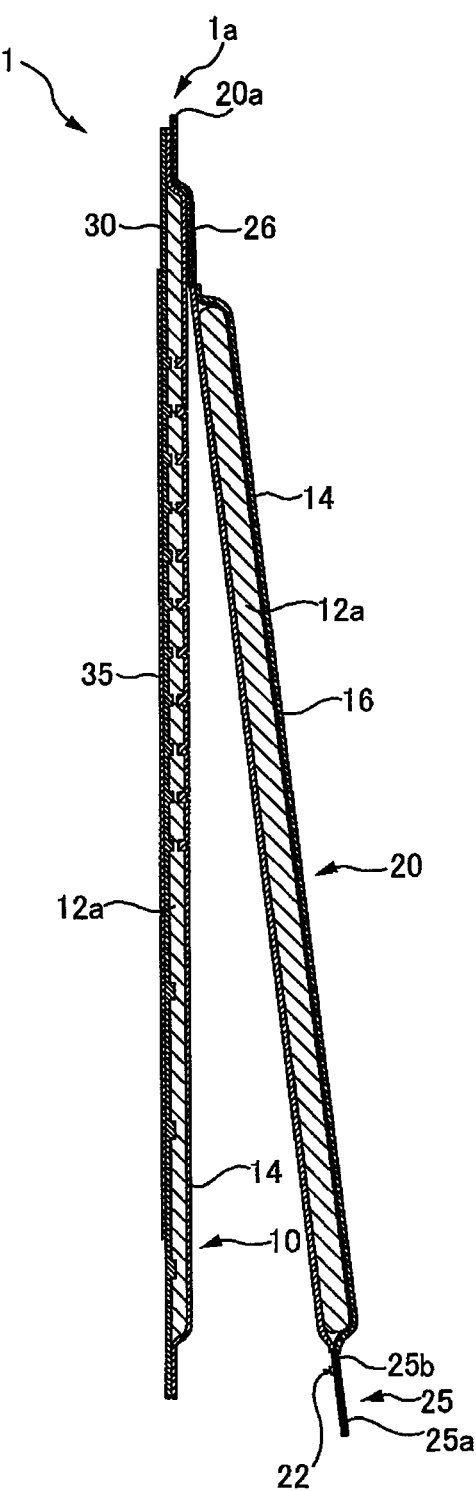
FIG. 4 is a cross-sectional view taken along line Y-Y in FIG. 1.
Figure 5:
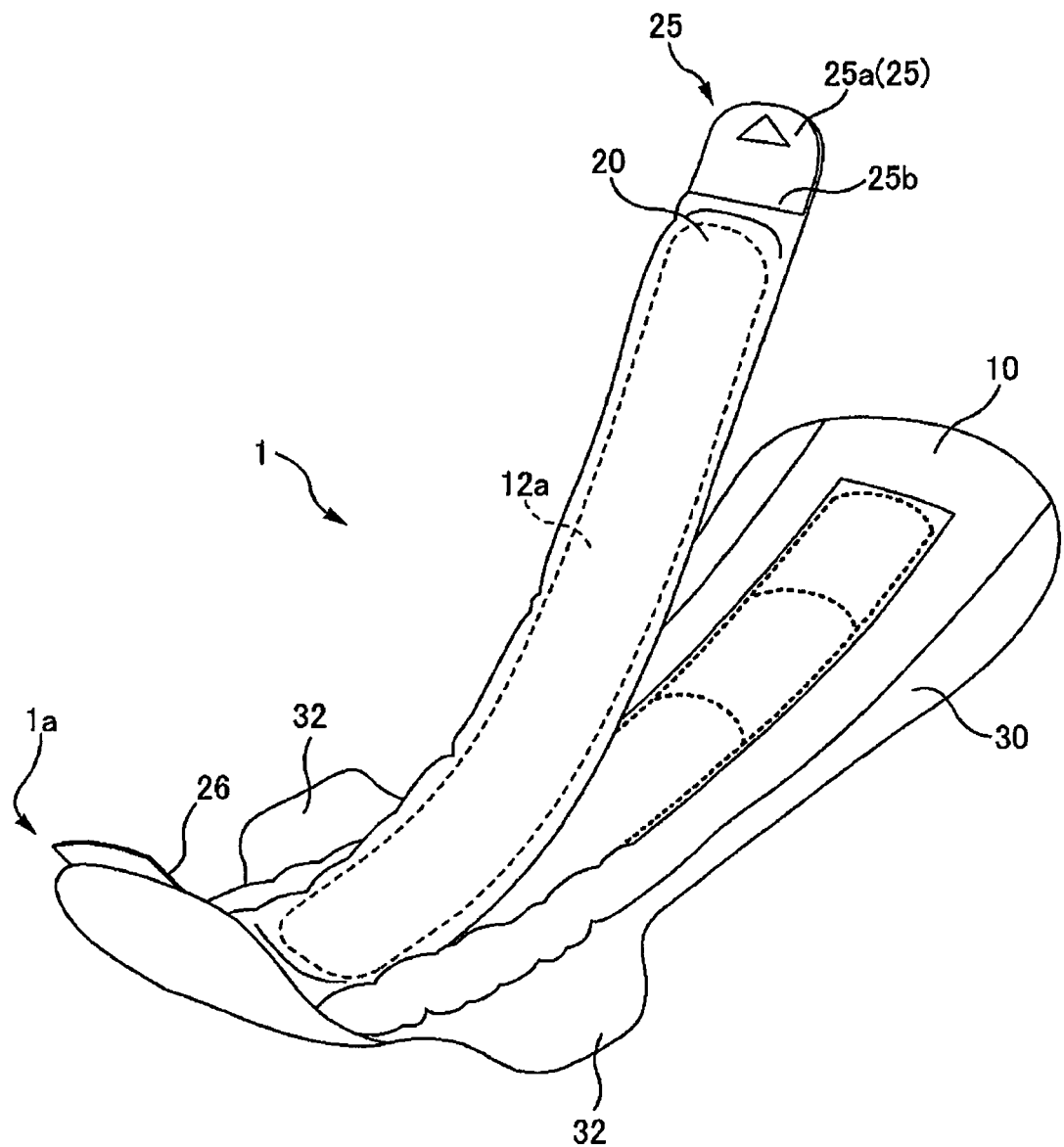
FIG. 5 is a perspective view showing the absorbent article according to the present embodiment.
Figure 6:
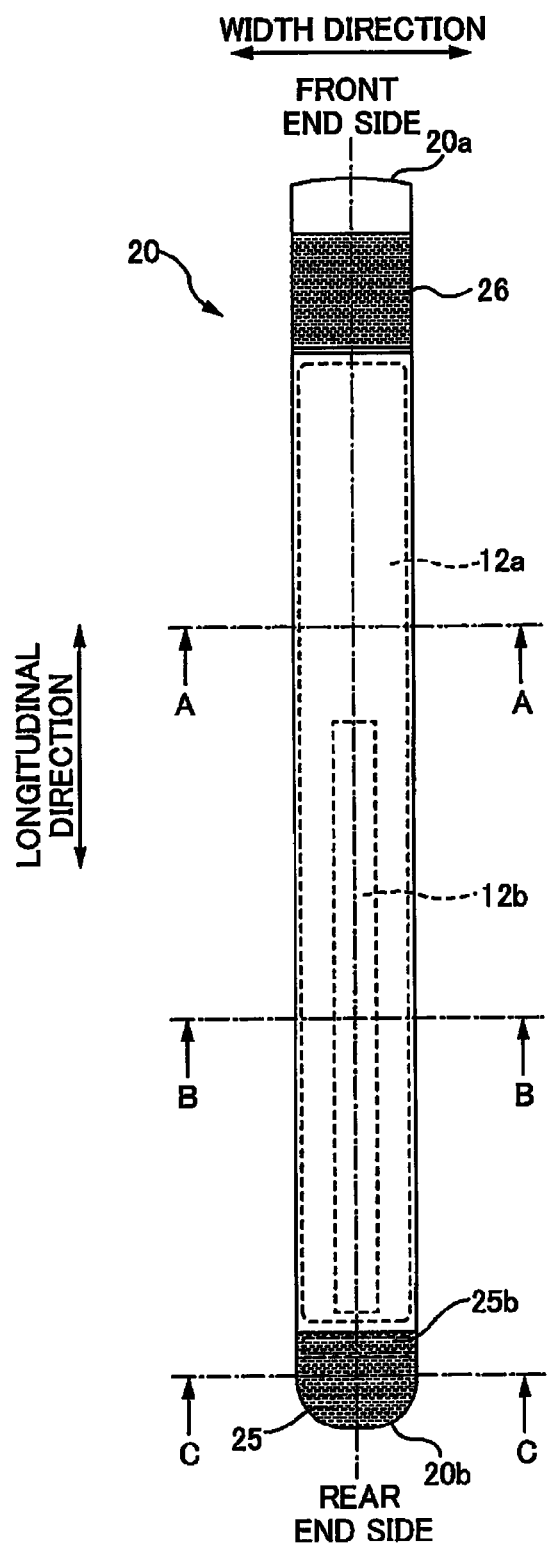
FIG. 6 is a plan view showing a top absorbent body.

FIG. 1 is a plan view showing the surface side of the absorbent article according to the present embodiment. FIG. 2 is a view showing the back face side of the absorbent article according to this embodiment. FIG. 3 is a cross-sectional view taken along line X-X in FIG. 1. FIG. 4 is a cross-sectional view taken along line Y-Y in FIG. 1. FIG. 5 is a perspective view showing the absorbent article according to this embodiment. FIG. 6 is a plan view showing a top absorbent body. FIG. 7(a) is a cross-sectional view taken along line A-A in FIG. 6. FIG. 7(b) is a cross-sectional view taken along line B-B in FIG. 6. FIG. 7(c) is a cross-sectional view taken along line C-C in FIG. 6.

As shown in the figures, an absorbent article 1 in this embodiment is elongated in a predetermined direction. The absorbent article 1 includes, a base absorbent body 10 as a substantially rectangular shaped absorbent article main body for absorbing fluid such as menstrual blood, a back face sheet 30 provided on the back face of the base absorbent body 10, and a top absorbent body 20 as an absorbent body that is joined to the surface of the base absorbent body 10 and disposed in the center in the width direction of the base absorbent body 10 that intersects the longitudinal direction. The back face sheet 30 is provided in order to prevent leakage of fluid that is to be absorbed by the base absorbent body 10 and the top absorbent body 20 to the back face side. Note that, round sealing processing for thermocompression-bonding an outer peripheral section of the absorbent article 1 is performed. In this embodiment, an opposing side of the top absorbent body 20 that opposes the base absorbent body 10 corresponds to the back face side of the top absorbent body 20, and a non-opposing side of the top absorbent body 20 that does not oppose the base absorbent body 10 corresponds to the surface side.

In the absorbent article 1 of this embodiment, a position Z assumed to contact against the bodily discharge opening portion, at which the bodily discharge opening portion is assumed to contact against the absorbent article 1, is positioned closer to the front end side than the center in the longitudinal direction, and on the center line in the width direction of the absorbent article 1. More specifically, the absorbent article 1 is formed such that the length from the position Z assumed to contact against the bodily discharge opening portion to the rear end side is longer than the length from the position Z assumed to contact against the bodily discharge opening portion to the front end side.

The base absorbent body 10 includes an absorbent body base material 12 as another absorbent body in the form of a sheet having a predetermined thickness, in which an absorbent body material 12a that has pulverized pulp obtained by pulverizing sheet-like pulp, a superabsorbent polymer, and a thermofusing fiber is wrapped in thin paper (not shown) such as tissue paper, and a surface sheet 14 that is attached to the surface of a center section in the width direction of the absorbent body base material 12. Both of the thin paper and the surface sheet 14 are fluid-permeable sheets. Furthermore, the thin paper is a sheet having openings that are smaller than particles of the superabsorbent polymer, and prevents the superabsorbent polymer from leaking outside of the absorbent body base material 12. A sheet that is softer than the thin paper is used as the surface sheet 14, since it is positioned on the surface side that contacts with the body.

The width of the top absorbent body 20 is formed narrower than the base absorbent body 10, and the length of the top absorbent body 20 in the longitudinal direction is formed slightly longer than that of the base absorbent body 10. The top absorbent body 20 includes, as in the base absorbent body 10, the absorbent body material 12a as an absorbent member, which is made of pulverized pulp, a superabsorbent polymer, and a thermofusing fiber. A fluid-permeable intermediate sheet 16 that has higher fluid retentivity than the surface sheet 14 is provided on the surface side of the top absorbent body 20 that contacts with the body. The intermediate sheet 16 is a member that has a higher density than the surface sheet 14 and is highly absorbent due to surface tension. By including the intermediate sheet 16 inside the surface sheet 14, fluid that has permeated the surface sheet 14 is moved toward the intermediate sheet 16 that sucks more fluid than the surface sheet 14.

Figure 7:
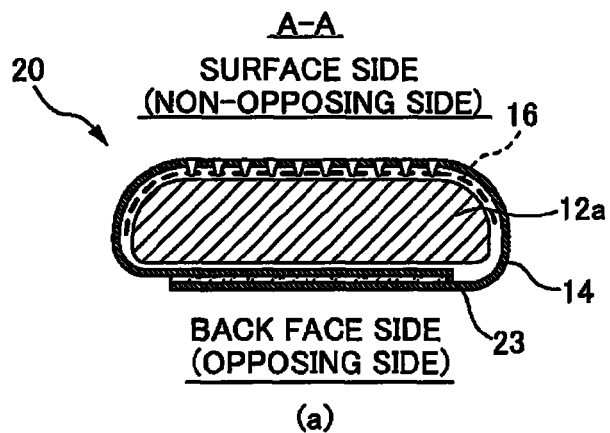
FIG. 7(a) is a cross-sectional view taken along line A-A in FIG. 6.
FIG. 7(b) is a cross-sectional view taken along line B-B in FIG. 6.
FIG. 7(c) is a cross-sectional view taken along line C-C in FIG. 6.
Figure 7:
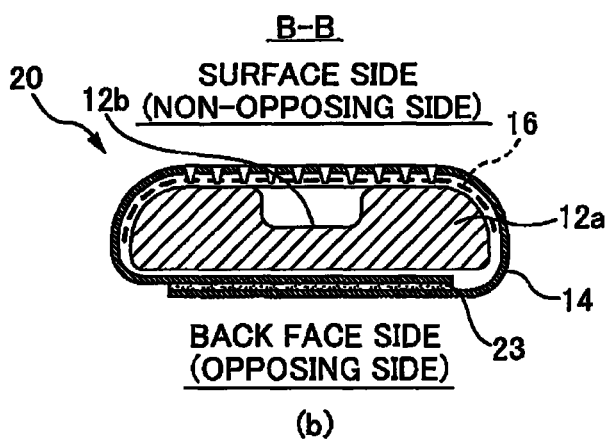
Figure 7:
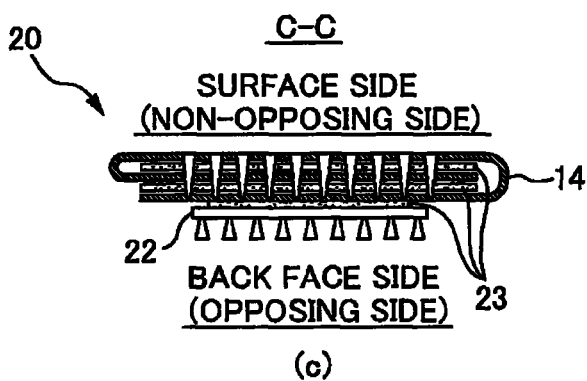
Figure 9:
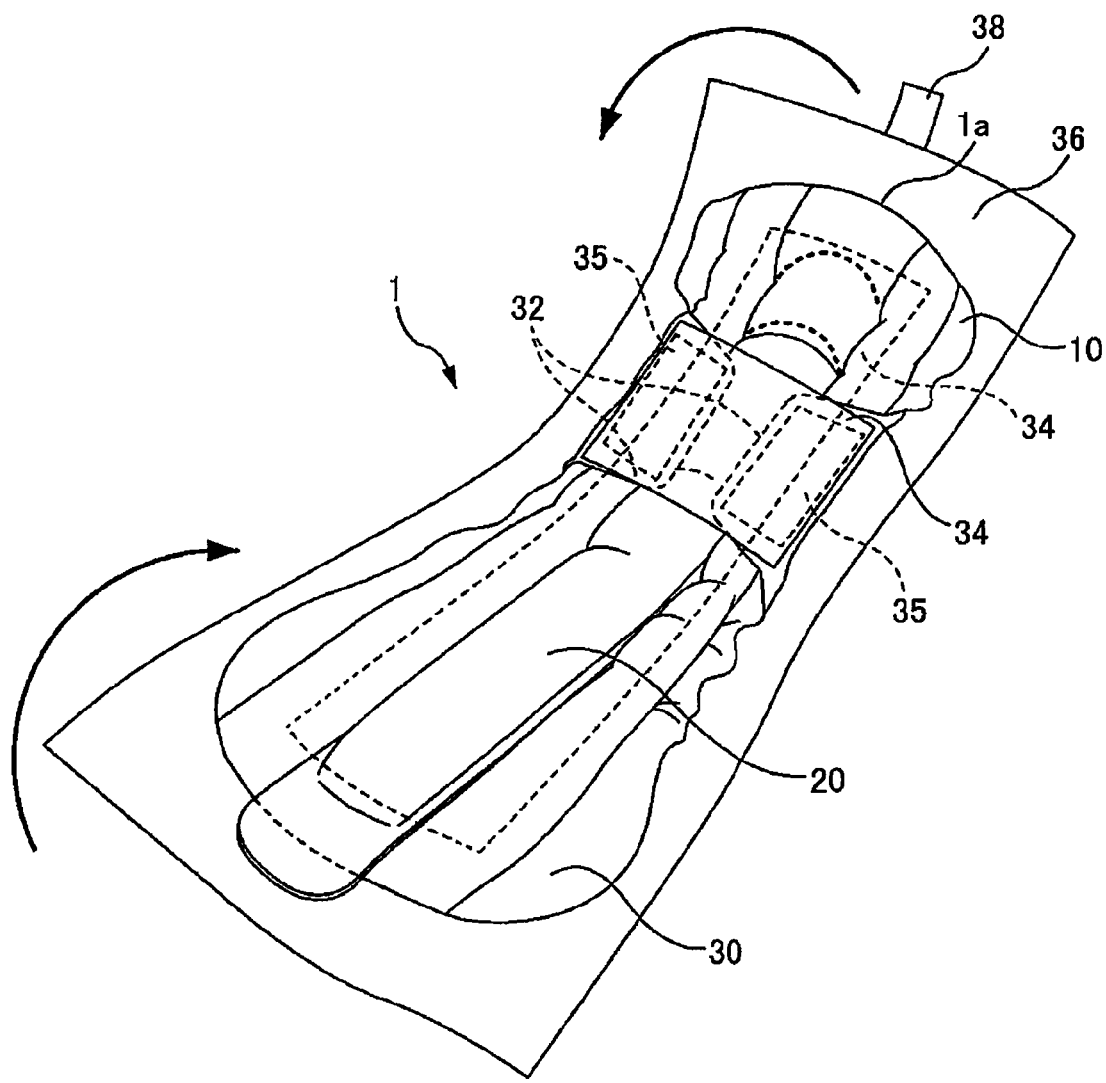
FIG. 9 is a perspective view showing a state of the absorbent article before use.

The absorbent body material 12a and the intermediate sheet 16 are wrapped in the surface sheet 14 serving as a sheet member in such a manner that the surface sheet 14 is wrapped around the absorbent body material 12a and the intermediate sheet 16 in the width direction, which intersects the longitudinal direction, from the surface side that is provided with the intermediate sheet 16 and that comes into contact with the body. Parts of the wrapped-around surface sheet 14 are overlapped on the back face side of the absorbent body material 12a, and the overlapping parts are adhered to each other via an adhesive 23. As a result, the back face side of the top absorbent body 20 will have high stiffness, and the surface sheet 14 on the back face side of the top absorbent body 20 is suppressed from being expanded/contracted in the width direction, because the surface sheet 14 has the overlapping parts on the back face side of the top absorbent body 20 and furthermore the overlapping parts are adhered to each other. More specifically, the top absorbent body 20 is formed so that a section on the surface side is more easily elongated than a section on the back face side. In FIGS. 4, 7, and 9, the intermediate sheet 16 is shown by a thick line or a thick broken-line for convenience.

Furthermore, as shown in FIG. 7(b), in a center section in the width direction of the top absorbent body 20, a thin-walled section 12b in which the amount of the absorbent body material 12a is less than that in other portions is formed in a rear end side region that is substantially half the top absorbent body 20 so as to extend along the longitudinal direction.

Furthermore, in a front end 20*a* section and a rear end 20*b* section of the top absorbent body 20, reinforced sections 25 and 26 are formed that have been reinforced by folding only the surface sheet 14 and performing embossing in a state where an adhesive 23 is interposed between the folded parts of the surface sheet 14. The reinforced sections 25 and 26 do not contain the absorbent body material 12*a* or the intermediate sheet 16.

Furthermore, a hook member 22 for fixing the rear end 20*b* side of the top absorbent body 20 to an undergarment in use is provided in a position of the top absorbent body 20 that is in a section 25*b* on the absorbent body material 12*a* side of the reinforced section 25, which is formed on the rear end 20*b* side of the top absorbent body 20, and that opposes the base absorbent body 10. The hook member 22 is, for example, a male member of a mechanical fastener.

The top absorbent body 20 is disposed on the base absorbent body 10 with the longitudinal direction of the top absorbent body 20 being set along the longitudinal direction of the base absorbent body 10. The front end 20*a* side, which is one of the end sections, of the top absorbent body 20 is permanently joined to the base absorbent body 10 by compression-bonding with a hot-melt adhesive interposed between the reinforced section 26 and the base absorbent body 10, and the rear end 20*b* side, which is the other end section, is formed so that it can be moved apart from the base absorbent body 10. Furthermore, before use, the reinforced section 25 on the rear end 20*b* side of the top absorbent body 20 is temporarily joined to the base absorbent body 10 by compression-bonding with no adhesive interposed therebetween. Herein, the permanent joining refers to a state in which the top absorbent body 20 and the base absorbent body 10 are firmly joined to each other in such a manner that at least one of the top absorbent body 20 and the base absorbent body 10 is inevitably damaged in the case where they are to be separated from each other intentionally. The temporary joining refers to a state in which the base absorbent body 10 and the top absorbent body 20 are joined to each other in such a manner that the user can easily detach and separate the top absorbent body 20 from the base absorbent body 10 without impairing the function of the base absorbent body 10 and the top absorbent body 20.

In the state where the top absorbent body 20 is temporarily joined to the base absorbent body 10, the rear end 20*b* of the top absorbent body protrudes rearward from the rear end of the base absorbent body 10. A section in which the reinforced section 25 is protruding from the base absorbent body 10 serves as a grasping section 25*a* that is to be picked up by the user at the time, for example, the absorbent article 1 is worn. The section where the base absorbent body 10 and the reinforced section on the side of the rear end 20*b* of the top absorbent body 20 overlap is compression-bonded by embossing and temporarily joined to each other. However, the hook member 22 also functions to temporarily join the rear end 20*b* side of the top absorbent body 20 and the surface sheet 14 of the base absorbent body 10 before use. In the description above, the hook member 22 was used for temporary joining, but the method for temporary joining is not limited to this. The method for temporary joining may be merely compression-bonding by embossing, or adhesion instead of using the hook member 22.

The back face sheet 30 is a thermoplastic and fluid-impermeable sheet of polyethylene, polypropylene, or the like. The back face sheet 30 is formed sufficiently wider than the base absorbent body 10. Furthermore, on both sides in the width direction of the back face sheet 30, holding sections 32 extended outward in the width direction are formed in a predetermined region in which the position Z assumed to contact against the bodily discharge opening portion is centered in the longitudinal direction. On the back face side of the back face sheet 30, in the vicinity of the region where the surface side has the base absorbent body 10 and in the holding sections 32, release sheets 34 (FIG. 2, FIG. 9) are provided via adhesives 35.

At the time of using the absorbent article 1, the release sheets 34 are removed, and the back face sheet 30 is made to contact against the inner side of an undergarment. Also, the holding sections 32 are folded outward, and are made to contact against the outer face of the undergarment. With the adhesives 35 interposed between the back face sheet 30 and the undergarment, the absorbent article 1 is held on the undergarment. Note that, since a release agent has been applied to the release sheets 34, the release sheets 34 can be easily removed from the back face sheet 30 in a state in which the adhesives 35 are left on the back face sheet 30.

In this embodiment, the back face sheet 30 as a sheet member was a thermoplastic and fluid-impermeable sheet made of polyethylene, polypropylene or the like. However, the back face sheet 30 also may be a sheet-like member containing the thermoplastic and fluid-impermeable sheet, for example, formed by layering thin paper, nonwoven fabric, or the like.

Figure 8:
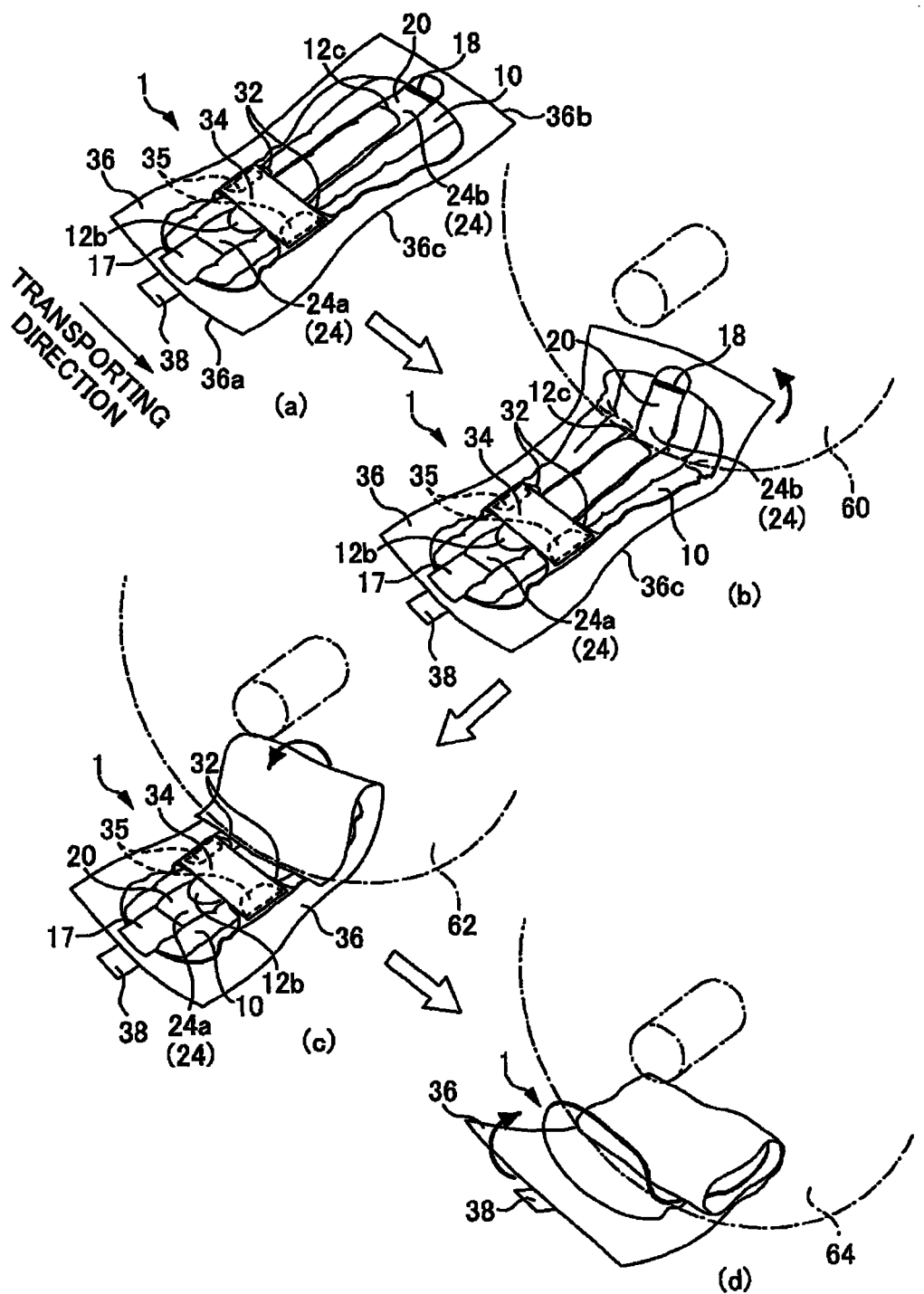
FIG. 8(a) is a view showing a state of the absorbent article before being folded.
FIG. 8(b) is a view showing the absorbent article being bent at a first folding position.
FIG. 8(c) is a view showing the absorbent article being bent at a second folding position.
FIG. 8(d) is a view showing the absorbent article being bent at a third folding position.

Next, the absorbent article 1 in a wrapped form will be described. FIGS. 8(*a*) to 8(*d*) are views for illustrating steps of folding the absorbent article to be wrapped. FIG. 8(*a*) is a view showing a state of the absorbent article before being folded, FIG. 8(*b*) is a view showing the absorbent article that is being bent at a first folding position, FIG. 8(*c*) is a view showing the absorbent article that is being bent at a second folding position, and FIG. 8(*d*) is a view showing the absorbent article that is being bent at a third folding position.

In the absorbent article 1, the holding sections 32 are bent toward the surface side, and the release sheets 34 covering the adhesives 35 are included on the holding sections 32 of both sides and the back face side respectively. The absorbent article 1 on which the release sheets 34 have been placed is, together with the rectangular wrapping sheet 36 disposed on the back face side, folded at three positions in the longitudinal direction while being transported. At that time, the base absorbent body 10 and the top absorbent body 20 overlapped with each other are folded in such a manner that these absorbent bodies are bent toward the surface side so that the top absorbent body 20 is positioned on the inner side.

Specifically, at the time of being folded, the absorbent article 1 and the wrapping sheet 36 are transported on a transporting table (not shown) with the longitudinal direction thereof being set to intersect the transporting direction. At the first folding position, the absorbent article 1 and the wrapping sheet 36 being transported are sandwiched between a first disk 60 that rotates about a shaft extending along a direction intersecting the transporting direction and the transporting table, and bent upward from the first folding position with a guide member (not shown) provided closer to the rear end side of the absorbent article 1 than the first disk 60. The guide member is formed in such a manner that the bending angle increases from the vicinity of the first disk 60 toward the front side in the transporting direction, and the absorbent article 1 and the wrapping sheet 36 are bent upward at gradually increasing angles while being transported, and thus folded.

The absorbent article 1 and the wrapping sheet 36 that have been folded at the first folding position are transported to a position at which a second disk 62 is disposed in alignment with the second folding position. Then, the absorbent article 1 and the wrapping sheet 36 are sandwiched between the second disk 62 and the transporting table and bent upward from the second folding position by a guide member (not shown) provided on the folded side with respect to the second disk 62. The guide member is formed such that the bending angle increases from the vicinity of the second disk 62 toward the front side in the transporting direction, and the absorbent article 1 and the wrapping sheet 36 are bent upward at gradually increasing angles while being transported, and thus folded. The absorbent article 1 and the wrapping sheet 36 that have been folded at the second folding position are transported to a position at which a third disk 64 is disposed in alignment with the third folding position. Then, the absorbent article 1 and the wrapping sheet 36 are sandwiched between the third disk 64 and the transporting table and bent upward from the third folding position by a guide member (not shown) provided on the front end side of the absorbent article with respect to the third disk 64. The guide member is formed such that the bending angle increases from the vicinity of the third disk 64 toward the front side in the transporting direction, and the absorbent article 1 and the wrapping sheet 36 are bent upward at gradually increasing angles while being transported, and thus folded.

In this manner, through the three bending steps, the absorbent article 1 is folded and wrapped in the wrapping sheet 36. Then, an end section of the wrapping sheet 36 on the side of a rear end 1b of the absorbent article 1 (hereinafter, referred to as a rear end 36b of the wrapping sheet 36) is extended to be longer than the absorbent article 1, and an adhesive has been slightly applied to that end section. When the wrapping sheet 36 is bent together with the absorbent article 1, the end section adheres with very weak adhesion to the side without treatment for detachment of the release sheet 34 provided on the holding sections 32 that have been folded toward the surface side of the top absorbent body 20. A lead tape 38 provided on the side of a front end 36a in the wrapping sheet 36 is attached to the outer face of the wrapping sheet 36 on the side of the rear end 36b that has already been bent together with the absorbent article 1. The wrapping sheet 36 that has been folded together with the absorbent article 1 is sealed by causing edge sections 36c in the longitudinal direction to adhere, and the absorbent article 1 that is contained in the wrapping sheet 36 in the form of a package is supplied to the user.

FIG. 9 is a perspective view showing a state of the absorbent article before use.

The absorbent article 1 is supplied to the user in a state where it is contained in the wrapping sheet 36, and when the user removes the lead tape 38 and opens the wrapping sheet 36, the front end 1a of the absorbent article 1 is exposed. When the exposed front end 1a of the absorbent article 1 is peeled from the wrapping sheet 36 having the lead tape 38, the absorbent article 1 can be easily taken out.

The absorbent article 1 that has been taken out is disposed at an appropriate position on an undergarment after the release sheet 34 on the back face side is removed. Then, the release sheet 34 on the holding sections 32 is removed, and the holding sections 32 are bent toward the undergarment side and attached to the outer side of the undergarment with the adhesives 35, and thus the absorbent article 1 is fixed to the undergarment. After the undergarment to which the absorbent article 1 is fixed is pulled up toward the body, a grasping section 25a is grasped and the top absorbent body 20 is pulled up by the user. Accordingly, the temporary joining between the base absorbent body 10 and the top absorbent body 20 is released, and the rear end 20b side of the top absorbent body 20 is spaced apart from the base absorbent body 10.

Subsequently, when the user moves the grasping section 25a in the longitudinal direction (substantially the vertical direction), the position of the top absorbent body 20 is adjusted in such a manner that the top absorbent body 20 is in close contact with the bodily groove at the bodily discharge opening portion and its vicinity. In a state that the position of the top absorbent body 20 has been adjusted, the top absorbent body 20 is bent and fixed at the skin-side surface of the back body of the undergarment or at an edge section of the undergarment. Accordingly, by disposing the top absorbent body 20 in close contact with the body of the user from the front side to the rear side along the bodily groove, the top absorbent body 20 is positioned so as to preferably come into contact against the body. The base absorbent body 10 is positioned substantially outside and below the bodily groove.

Regarding the absorbent article 1 as described above in which the base absorbent body 10 and the top absorbent body 20 are overlapped and joined to each other on the front end 20a side in the longitudinal direction, when the absorbent article 1 is to be used with the top absorbent body 20 sandwiched in the groove of the buttocks or the like of the human body, by pulling up the rear end 20b of the top absorbent body 20 so that the top absorbent body 20 enters into the groove of the buttocks of the human body, the narrower the top absorbent body 20 is, the easier the top absorbent body 20 is to be sandwiched in the groove of the buttocks or the like. However, the absorbent article is used essentially for the purpose of absorbing menstrual blood, and thus in a case where the width of the top absorbent body 20 is narrow, the absorption capacity gets smaller. Moreover, in the case where the width of the top absorbent body 20 that is seen by the user is narrow when the wrapped absorbent article 1 is opened, a sense of insecurity about leakage of menstrual blood may be given to the user. Therefore, in the absorbent article 1 of the foregoing embodiment, the width of the top absorbent body 20 before use, that is, in a state where the package is opened, is made wider than that when worn, and the top absorbent body 20 is configured so that the width thereof becomes narrower by being bent in the width direction when worn.

However, there is a risk that a top absorbent body that is formed so that the width thereof before use is wider than the width at wearing cannot be appropriately sandwiched in the groove of the buttocks or the like simply by pulling up the rear end section. To address this problem, the absorbent article 1 of this embodiment has a configuration in which the surface sheet 14 that wraps the absorbent body material 12a and the intermediate sheet 16 of the top absorbent body 20 is wrapped around the absorbent body material 12a and the intermediate sheet 16 from the surface side in the width direction intersecting the longitudinal direction, and parts of the surface sheet 14 are overlapped on the back face side and attached to each other via the adhesive 23. With this configuration, the stiffness of a section on the back face side of the top absorbent body 20 becomes higher than that of a section on the surface side, and the section on the surface side is more easily elongated than the section on the back face side.

Figure 10:
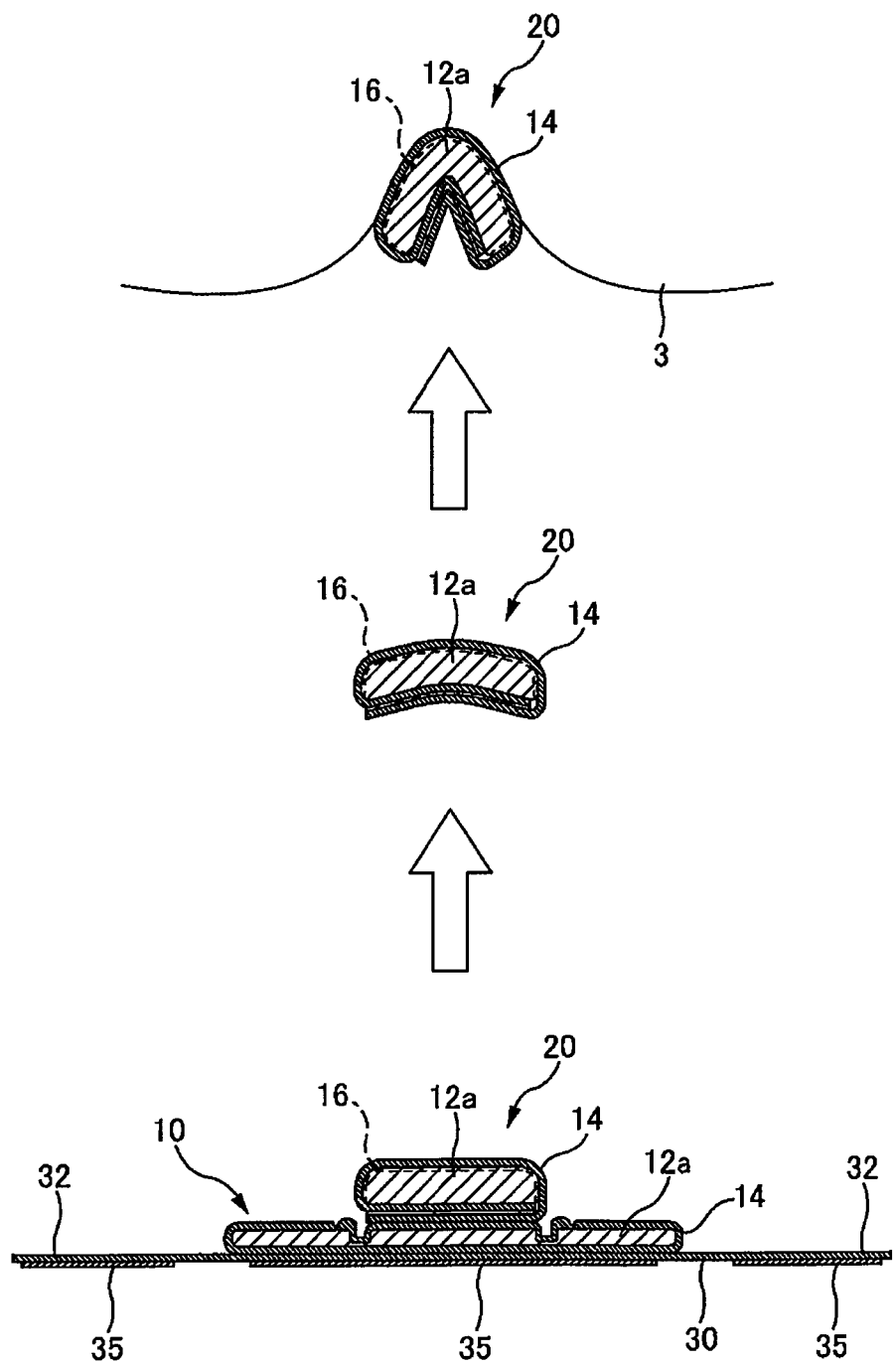
FIG. 10 is a view for illustrating the manner in which the absorbent article is worn.

FIG. 10 is a view for illustrating the manner in which the absorbent article is worn.

As shown in FIG. 10, by pulling up the top absorbent body 20 with the rear end 20b section that is temporarily joined to the base absorbent body 10, the rear end 20b is separated from the base absorbent body 10. Then, when the top absorbent body 20 is positioned along the bodily groove, the top absorbent body 20 enters the inside of the groove while being bent. At this time, since the groove of the body (the buttocks) is recessed, by lifting up the top absorbent body 20, the top absorbent body 20 is protruded (mountain-folded) corresponding to the recess of the groove. However, although there are variations among individuals, the buttocks are soft. Thus, if the top absorbent body 20 itself cannot be flexibly deformed into a protruded shape corresponding to the bodily recess, the top absorbent body 20 contacts against the buttocks as a flat surface and thus pushes up the flesh on both sides of the groove. Accordingly, it becomes difficult for the top absorbent body 20 to advance into the bodily recess (groove). For this reason, it is preferable that the surface side of the top absorbent body 20 is easily elongated compared with the back face side so that by being pulled up the top absorbent body 20 can advance into the groove while being flexibly deformed into a protruded shape corresponding to the recess of the soft buttocks.

Moreover, in the center section in the width direction of the top absorbent body 20, the thin-walled section 12b is formed along the longitudinal direction in the rear end side 20b region that is substantially half the top absorbent body. Thus, the top absorbent body 20 can be bent at substantially the center in the width direction thereof so that the surface side forms a continuous peak along the longitudinal direction. As a result, the absorbent body material 12a of the top absorbent body 20 can be disposed substantially evenly with respect to the bodily groove. Then, since the absorbent body material 12a is disposed substantially evenly with respect to the groove, unevenness of the menstrual blood that is absorbed by the bent absorbent body material 12a hardly occurs, and thus more menstrual blood can be absorbed.

More specifically, according to the absorbent article 1 of this embodiment, by forming the width of the top absorbent body 20 before use wider than that when worn, the absorption capacity can be made larger than that of an absorbent body that originally has a narrow width so as to fit in the bodily groove, and at the same time, a sense of security regarding the absorption capacity can be given to the user. At this time, by forming the top absorbent body 20 so that a section on the surface side is more easily elongated than a section on the back face side, the top absorbent body 20 when worn can be bent to form a peak and can be easily and reliably placed in the buttocks 3.

Regarding the ease of elongating of the section on the surface side of the top absorbent body 20 and the section on the back face side, which is suitable for the absorbent article 1 of this embodiment, for example, it is desirable that the 5% elongation strength in the width direction on the surface side of the surface sheet 14 is equal to or less than 80% of the 5% elongation strength in the width direction on the back face side, and furthermore, the 5% elongation strength in the width direction on the surface side of the surface sheet 14 is less than 3 N/25 mm. Herein, 5% elongation strength is a value indicating the load in the case where the surface sheet 14 is elongated 5% by stretching. Moreover, the reason why the reference value is expressed by the 5% elongation strength in the width direction is as follows. In the case where the top absorbent body 20 to be inserted into the bodily groove is deformed into a protruded shape that protrudes to the surface side, a surface layer on the skin side (the surface side) is elongated more than a surface layer on the non-skin side (the back face side) by about 3% to 20%. In other words, the surface layer on the skin side is required to have a lower tensile strength at a relatively low elongation than the surface layer on the non-skin side. Moreover, consideration is also given to an issue that in the case where the 5% elongation strength in the width direction is equal to or more than 3 N/25 mm, it is difficult for the top absorbent body 20 to deform so as to protrude to the surface side when placed in the bodily groove, and there is a risk that an uncomfortable feeling will be given to the user. Accordingly, it can be considered that by setting the 5% elongation strength in the width direction on the surface side of the surface sheet 14 to equal to or less than 80% of the 5% elongation strength in the width direction on the back face side, and furthermore, by setting the 5% elongation strength in the width direction on the surface side of the surface sheet 14 to less than 3 N/25 mm, a distinct difference is produced between the surface side and the back face side, and thus the top absorbent body 20 can be easily bent so as to protrude to the surface side.

Preferably, by setting the 5% elongation strength in the width direction on the surface side of the surface sheet 14 to equal to or less than 60% of the 5% elongation strength in the width direction on the back face side, and furthermore, by setting the 5% elongation strength in the width direction on the surface side of the surface sheet 14 to less than 2 N/25 mm or to less than 1.2 N/25 mm, the top absorbent body 20 can be even more easily bent so as to protrude to the surface side. Furthermore, it is more preferable that the elongation strength in the case where the surface sheet 14 is elongated 0% to 20% in the width direction is less than 3 N/25 mm.

As the material that achieves the elongation strength as described above and that reflects consideration of the touch to the skin, for example, an air-through nonwoven fabric is preferable, and the air-through nonwoven fabric preferably has a weight ranging from 20 to 80 g/m$^2$. However, this is not limited to such. Moreover, the entire surface layer on the skin side of the surface sheet 14 may not have the elongation strength within the above-described numerical range, or the surface layer may be partly provided with a section having a low tensile strength. For example, a center section in the width direction of the top absorbent body 20 may be ribbed or grooved in advance, along the longitudinal direction, so as to be easily elongated in the width direction.

Furthermore, the configuration in which the top absorbent body 20 is easily bent so as to protrude to the surface side is especially suitable for the absorbent article 1 in which, as described above, the front end 20a section in the longitudinal direction of the top absorbent body 20 is undetachably joined to the base absorbent body 10, and the rear end 20b section is temporarily joined to the base absorbent body 10 in a detachable manner.

According to this absorbent article 1, the front end 20a of the top absorbent body 20 is permanently joined to the base absorbent body 10. Thus, it is possible to manufacture an absorbent article 1 that can be used in a state where the rear end 20b is detached from the base absorbent body 10, and the rear end 20b side is separated from the base absorbent body 10. Accordingly, this absorbent article 1 is more suitable for an absorbent article 1 that is used in a state where the top absorbent body 20 is separated from the base absorbent body 10 and placed in the groove of the buttocks 3. More specifically, this absorbent article 1 is especially suitable for the absorbent article 1 of this embodiment that is used in a state where the top absorbent body 20 is separated from the base absorbent body 10 and placed in the bodily groove rather than for an absorbent article in which the top absorbent body 20 and the base absorbent body 10 are merely overlapped.

Moreover, in the top absorbent body 20, the absorbent body material 12a is wrapped in the surface sheet 14. Thus, by overlapping parts of the surface sheet 14 wrapping the absorbent body material 12a on the back face side and adhering the overlapping parts together, the stiffness on the back face side of the top absorbent body 20 can be made higher than that on the surface side, without adding another member. Accordingly, the top absorbent body 20 that is easily bent to form a peak protruding to the surface side can be formed, simply by wrapping the absorbent body material 12a in the surface sheet 14.

Furthermore, in the top absorbent body 20, the thin-walled section 12b in which the thickness of the absorbent body material 12a is made thin is formed along the longitudinal direction. Thus, in the case where the top absorbent body 20 is pressed by the buttocks 3 or the like, the top absorbent body 20 can be bent in the width direction along the groove of the buttocks 3 and easily deformed so that the width thereof becomes narrow. Herein, since the thin wall section 12b is formed biased toward the rear end 20b side in the entire region in the longitudinal direction, the rear end 20b side can be bent even further and reliably placed in the groove of the buttocks 3, and the top absorbent body 20 can be brought into contact with the body in a relatively flat state in the vicinity of the discharge opening of menstrual blood. Accordingly, it is possible to provide an absorbent article 1 that further prevents leakage of menstrual blood. Furthermore, since the thin wall section 12b is provided in the center in the width direction, the top absorbent body 20 can be bent at the center in the width direction, the top absorbent body 20 can be disposed in a balanced manner in the width direction with respect to a discharge section of menstrual blood and the like and the groove, and thus menstrual blood and the like can be absorbed more efficiently.

In this embodiment, an example in which the thin-walled section 12b is provided was described. However, the thin-walled section 12b is not necessarily required, and the top absorbent body 20 that can be easily bent to form a peak protruding to the surface side can be formed by forming a section on the surface side of the top absorbent body 20 that is more easily elongated than a section on the back face side.

Modified Examples of the Top Absorbent Body

In the foregoing embodiment, a section on the surface side of the top absorbent body 20 was made to elongate more easily in the width direction than a section on the back face side, by the configuration in which parts of the surface sheet 14 wrapping the absorbent body material 12a and the intermediate sheet 16 of the top absorbent body 20 are overlapped on the back face side and adhered to each other via the adhesive 23. However, the method for realizing the configuration in which the section on the surface side of the top absorbent body is more easily elongated in the width direction than the section on the back face side is not limited to this.

Figure 11:
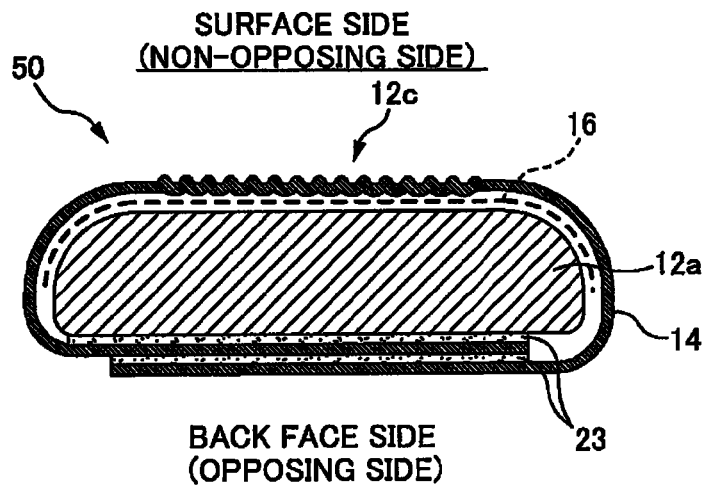
FIG. 11 is a view showing a first modified example of the top absorbent body.

FIG. 11 is a view showing a first modified example of the top absorbent body.

As shown in FIG. 11, in a top absorbent body 50, the surface sheet 14 that wraps the absorbent body material 12a, or the surface sheet 14 and the intermediate sheet 16 may be provided with wrinkles or so-called gathers 12c that will be elongated in the width direction. In this case, the gathers 12c provided in the top absorbent body 50 may be provided only on the surface side or may also be provided on the lateral sides and the back face side. However, by making a region where the gathers 12c are provided, in the width direction, wider in the section on the surface side than in the section on the back face side, the configuration is possible in which the section on the surface side of the top absorbent body 50 can be more easily elongated in the width direction than the section on the back face side.

Figure 12:
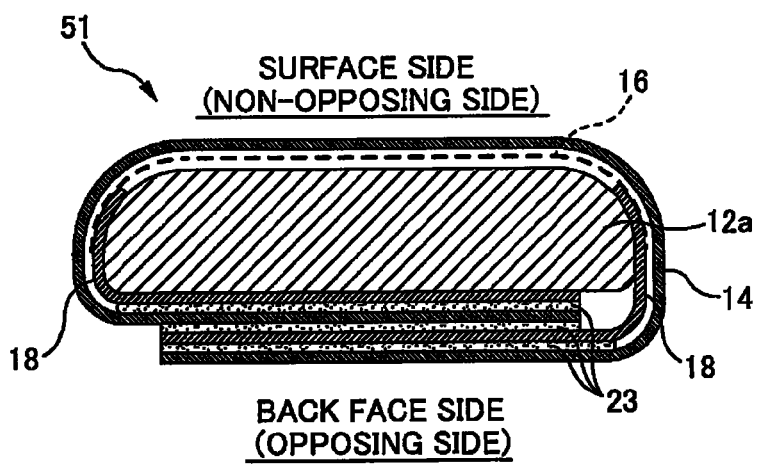
FIG. 12 is a view showing a second modified example of the top absorbent body.
Figure 13:
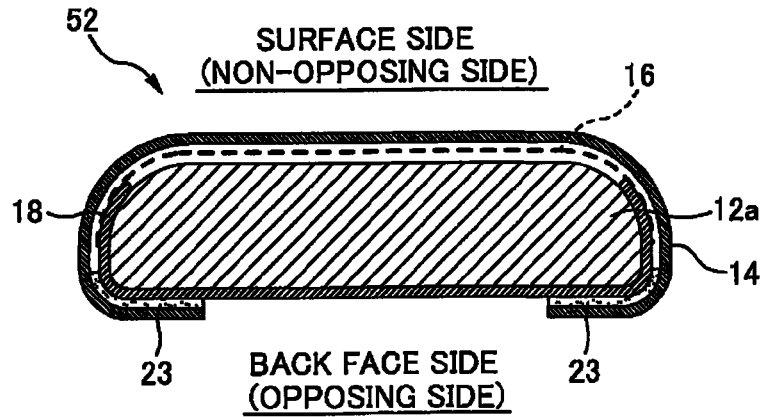
FIG. 13 is a view showing a third modified example of the top absorbent body.
Figure 14:
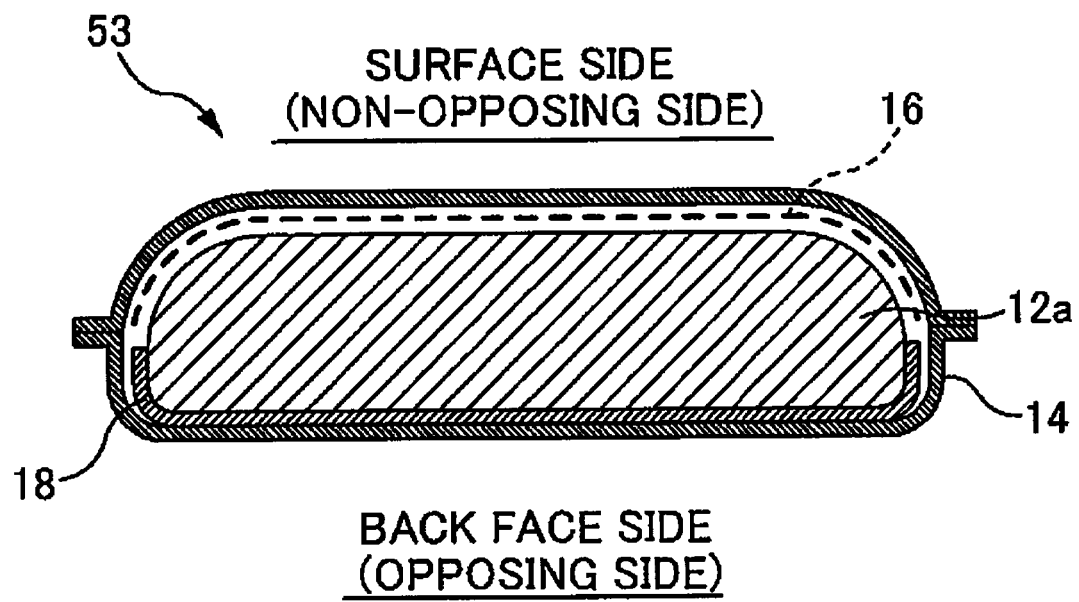
FIG. 14 is a view showing a fourth modified example of the top absorbent body.

Moreover, as shown in FIGS. 12 to 14, by providing the back face side of the top absorbent body with a leakage preventing sheet 18 for preventing fluid that has been absorbed by the top absorbent body from leaking out the back face side, the configuration is possible in which the section on the surface side is more easily elongated in the width direction than the section on the back face side.

FIG. 12 is a view showing a second modified example of the top absorbent body. FIG. 13 is a view showing a third modified example of the top absorbent body. FIG. 14 is a view showing a fourth modified example of the top absorbent body.

The leakage preventing sheet 18 is, for example, a thermoplastic and fluid-impermeable sheet such as polyethylene, polypropylene, or the like similar to the back face sheet 30 provided on the back face of the base absorbent body 10, and has lower stretchability than the surface sheet 14 and the intermediate sheet 16 made of nonwoven fabric having high fluid permeability. The leakage preventing sheet 18 is not provided in a wide region on the surface side of the top absorbent body for functional reasons, but on the other hand, it is preferable that the leakage prevention sheet 18 is provided over the entire region on the back face side. Accordingly, top absorbent bodies 51, 52, and 53 as shown in FIGS. 12 to 14, in which the leakage preventing sheet 18 having lower stretchability than the surface sheet 14 and the intermediate sheet 16 is provided in a wider region on the back face side than on the surface side, have a configuration in which a section on the surface side is more easily elongated in the width direction than a section on the back face side.

In the configuration of the top absorbent body 51 shown in FIG. 12, in addition to the surface sheet 14, the leakage preventing sheets 18 are provided from an end section in the width direction on the surface side of the absorbent body material 12a to the vicinity of an end section in the width direction of the surface sheet 14. On the back face side of the absorbent body material 12a, the surface sheet 14 and the leakage preventing sheets 18 in an overlapped state wrap around the absorbent body material 12a in the width direction, and both end sections of the surface sheet 14 and the leakage preventing sheets 18 are overlapped and adhered to each other via an adhesive 23. In this case, the surface side of the top absorbent body 51 includes almost no region provided with a leakage preventing sheet, while on the back face side, two surface sheets 14 and two leakage preventing sheets 18 are overlapped over almost the entire region, and furthermore, these sheets are adhered to each other. Thus, the top absorbent body 51 can have a configuration in which the surface side thereof is easily elongated in the width direction compared with the back face side.

Moreover, in the top absorbent body 52 shown in FIG. 13, the leakage preventing sheet 18 provided on the back face side of the absorbent body material 12a is provided so as to wrap around the absorbent body material 12a up to the side sections thereof, and the surface sheet 14 provided on the surface side is provided so as to overlap end sections of the leakage preventing sheet 18 in the width direction, and both end sections of the surface sheet 14 and the leakage preventing sheet 18 are adhered to each other. Thus, the surface sheet 14 provided on the back face side exists only in very small regions in the width direction. In the case of this top absorbent body 52, the surface side of the top absorbent body 52 is configured so as to elongate more easily in the width direction compared with the back face side due to the difference in the stretch properties among the materials included in each of the surface sheet 14, the intermediate sheet 16, and the leakage preventing sheet 18. Therefore, the stiffness of a section on the back face side can be lowered than that in the case where the surface sheet 14 and the leakage preventing sheet 18 are overlapped on the back face side as in the above-described top absorbent body 51. In other words, it is possible to prevent the stiffness of a section on the back face side from becoming extremely higher than the stiffness of a section on the surface side.

Moreover, in the top absorbent body 53 shown in FIG. 14, surface sheets 14 respectively disposed on the surface side and the back face side of the absorbent body material 12a one by one are adhered to each other on the side sections of the absorbent body material 12a, and a leakage preventing sheet 18 is provided over the entire region between the surface sheet 14 disposed on the back face side and the absorbent body material 12a. In this case, due to the leakage preventing sheet 18 provided on the back face side of the top absorbent body 53, a section on the surface side can be configured to elongate more easily in the width direction than a section on the back face side. Herein, by adhering the surface sheet 14 on the back face side and the leakage preventing sheet 18, the surface side can be configured to elongate even more easily in the width direction compared with the back face side.

In the above-described first to fourth modified examples of the top absorbent body, there is no mention regarding the thin-walled section. However, it is possible to include the thin-walled section as in the case of the top absorbent body 20 of the foregoing embodiment in which the thin-walled section 12b is provided.

In the foregoing embodiment, the base absorbent body 10, as an absorbent article main body, includes the absorbent body base material 12 and the surface sheet 14. However, the absorbent article main body does not necessarily have to include the absorbent body base material 12.

Figure 15:
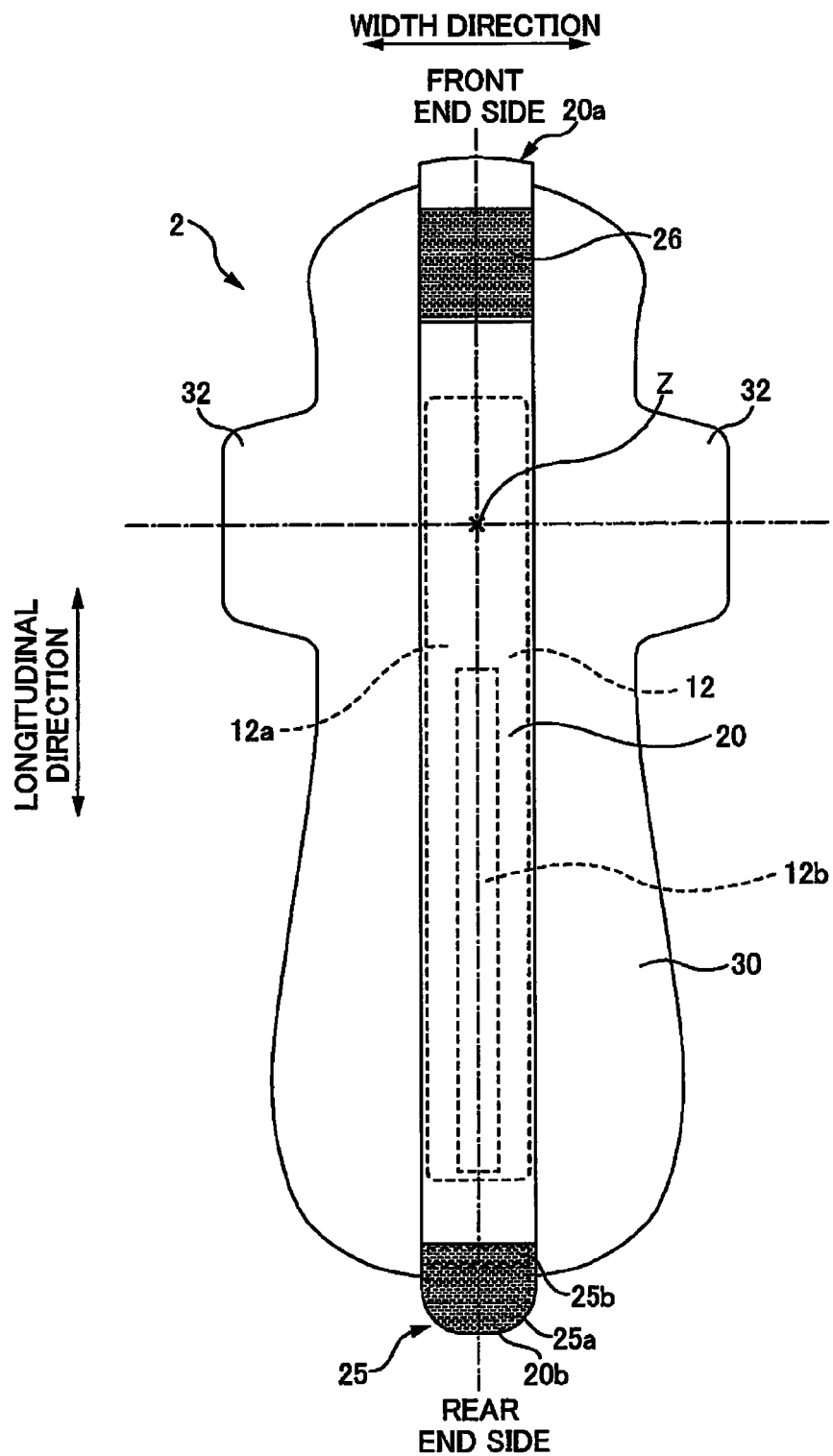
FIG. 15 is a plan view showing a first modified example of the absorbent article.

FIG. 15 is a plan view showing a first modified example of the absorbent article 1. For example, as shown in FIG. 15, an absorbent article 2 of the first modified example has a shape elongated in a predetermined direction. The absorbent article 2 includes a surface sheet 14 as an absorbent article main body, a back face sheet 30 as a sheet member, provided on the back face side as one of the faces of the surface sheet 14, that is for preventing fluid that is to be absorbed by a top absorbent body 20 from leaking to the back face side, and the top absorbent body 20 as an absorbent body, joined to the surface of the surface sheet 14 and disposed along the longitudinal direction in the center in the width direction of the surface sheet 14. Herein, the absorbent article main body is not only limited to the surface sheet 14, but the absorbent article main body may also be a member in which a sheet-like member is layered in addition to the surface sheet 14.

In the foregoing embodiment, the absorbent article 1 was described in which the front end 20a side of the top absorbent body 20 is permanently joined to the base absorbent body 10, and the top absorbent body 20 and the base absorbent body 10 are formed in an integrated manner. However, the top absorbent body 20 and the base absorbent body 10 may be temporarily joined to each other in a detachable manner, and the user may wear the absorbent article 1 in a state where the top absorbent body 20 is joined to the base absorbent body 10, or may remove the top absorbent body 20 and wear only the base absorbent body 10, as appropriate.

Figure 16:
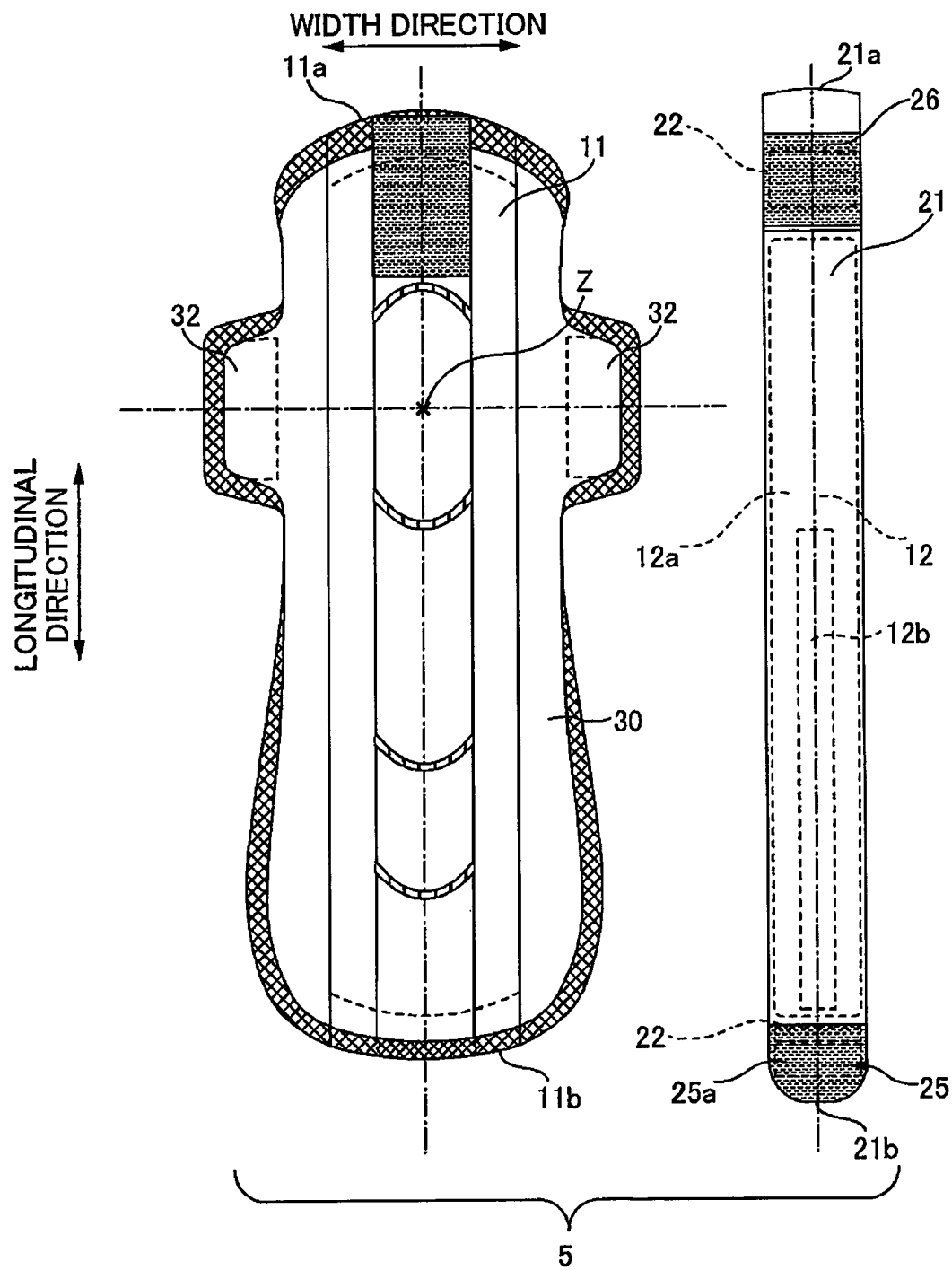
FIG. 16 is a plan view showing a second modified example of the absorbent article.
Figure 17:
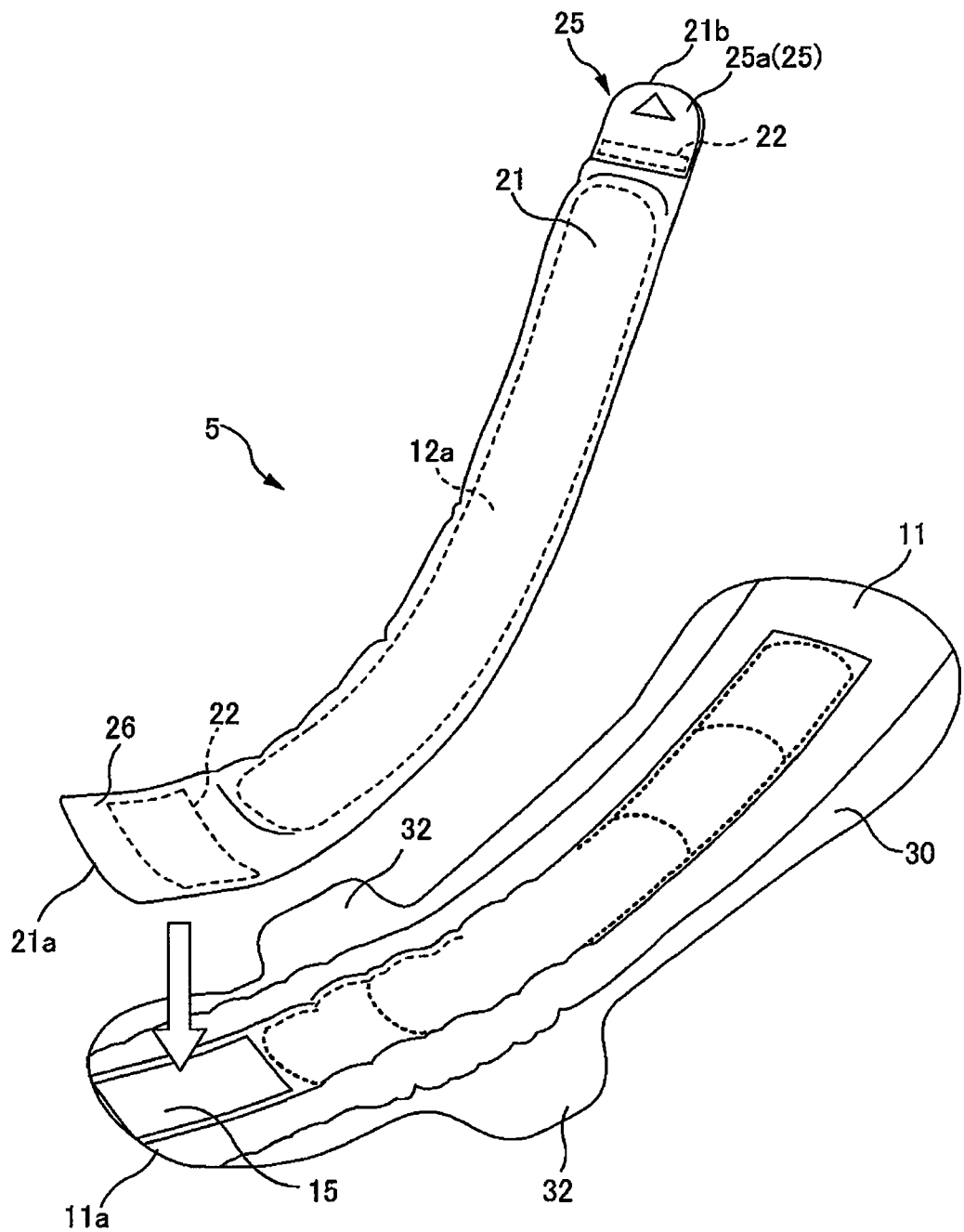
FIG. 17 is a perspective view showing the second modified example of the absorbent article.

FIG. 16 is a plan view showing a second modified example of the absorbent article. FIG. 17 is a perspective view for illustrating the second modified example of the absorbent article. In the following description, the same elements as in the foregoing embodiment are given the same reference numerals, and a repeated description thereof is omitted.

In an absorbent article 5 of the second modified example, not only sections of rear ends 11b and 21b but also sections of front ends 11a and 21a of a base absorbent body 11 and a top absorbent body 21 are temporarily joined to each other in a detachable manner.

Particularly, different from the top absorbent body 20 of the foregoing embodiment, the top absorbent body 21 has a hook member 22 provided in a section on the front end 21a side that faces the base absorbent body 11, as is the case with the rear end 21b side.

Moreover, different from the base absorbent body 10 of the foregoing embodiment, the front end side of the base absorbent body 11 is provided with a female member, for example, a loop member 15, of a mechanical fastener that can be joined to the hook member 22 provided in the top absorbent body 21.

Then, in the absorbent article 5 of the second modified example, the top absorbent body 21 is overlapped and disposed along the longitudinal direction of the base absorbent body 11. The hook member 22 on the front end 21a side of the top absorbent body 21 is joined to the loop member 15 on the front end 11a side of the base absorbent body 11, and the rear end 11b side of the base absorbent body 11 and the rear end 21b side of the top absorbent body 21 are temporarily joined to each other in the same manner as in the absorbent article 1 of the foregoing embodiment. Incidentally, the hook member 22 on the front end 21a side of the top absorbent body 21 can also be fixed to the surface sheet 14 of the base absorbent body 11 as is the case with the rear end 21b side. However, in some cases, a nonwoven fabric having a good texture is used for the surface sheet 14 in order to improve the feel. The cross strength of fibers of a nonwoven fabric having a good texture is low, and there is a risk that a high joining strength cannot be obtained. The absorbent article is worn with joining sections on the side of the front ends 15 and 21a of the base absorbent body 11 and the top absorbent body 21 remaining in a joined state at the time of use, and thus a joining strength higher than that on the side of the rear ends 11b and 21b is required. For this reason, the loop member 15 is used as the joining section on the front end 11a side of the base absorbent body 11, thereby securing a high joining strength with the top absorbent body 21 while allowing the base absorbent body 11 to be detachable from the top absorbent body 21.

Moreover, in the case where the top absorbent body 21 is removed, the joining position is indicated by the loop member 15. Thus, it is desirable to use a loop member 15 having, for example, a color tone different from that of the surface sheet 14 so that the user who is going to join the top absorbent body 21 to the base absorbent body 11 can visually find the joining position easily.

In the second modified example, an example in which the loop member 15 is provided on the base absorbent body 11 side, and the hook member 22 is provided on the top absorbent body 21 side was described. However, it is also possible that a male member such as the hook member 22 is provided on the base absorbent body 11 side, and a female member such as the loop member 15 is provided on the top absorbent body 21 side.

According to the absorbent article 5 of the second modified example, it is possible to choose to wear the absorbent article 5 in a state where the base absorbent body 11 and the top absorbent body 21 are joined to each other, or to wear the absorbent article 5 in a state where the top absorbent body 21 is removed from the base absorbent body 11 as necessary. For example, in the case where a large amount of fluid is to be absorbed, the absorbent article 5 can be used in a state where the base absorbent body 11 and the top absorbent body 21 are joined to each other with the top absorbent body 21 being placed in the groove of the buttocks, while in the case where a small amount of fluid is to be absorbed, the base absorbent body 11 can be used alone in a state where the top absorbent body 21 is removed from the base absorbent body 11. Therefore, it is possible to cope with variations in the amount of fluid to be absorbed by using the absorbent article 5 alone without preparing a plurality of types of absorbent articles.

Furthermore, an absorbent article may also be supplied to the user in which, instead of the loop member 15, an adhesive material is applied to the section of the base absorbent body 11 of the second modified example where the loop member 15 is provided, and such section is covered with a release sheet, and the top absorbent body 20 that is not joined to the base absorbent body 11 is overlapped and disposed on the release sheet. Even in this case, it is desirable that the color tone of the adhesive material is different from the color tone of the surface sheet 14. Moreover, an absorbent article may also be supplied to the user in which an adhesive material is applied to a section on the front end 20*a* side of the top absorbent body 20 that faces the base absorbent body 10 and such section is covered with a release sheet, and the top absorbent body 20 is overlapped and disposed on the base absorbent body in which a region that the top absorbent body 20 is to be fixed to is clearly marked. In this case, the absorbent article in a state where the top absorbent body 20 is overlapped on the base absorbent body 10 without being joined thereto undergoes a wrapping processing as illustrated in FIG. 8, and the top absorbent body 20 and the base absorbent body 10 that are separate from each other are wrapped in a single wrapping sheet 36 and supplied to the user.

In the foregoing embodiments, for the sake of convenience of the description, a configuration was described in which one absorbent body base material 12 is provided in the center in the width direction of the base absorbent body 10, but there is no limitation to this. For example, a configuration is possible in which side absorbent bodies are respectively provided, along the longitudinal direction, in both end sections in the width direction of the base absorbent body 10. Also, a configuration may be adopted in which, instead of the side absorbent bodies, standing gathers are respectively provided at both end sections.

Furthermore, in the foregoing embodiments, an example was described in which the exterior of the absorbent body material 12*a* and the intermediate sheet 16 of the top absorbent body is wrapped in the surface sheet 14, and the reinforced sections 25 and 26 are formed on both end sides of the top absorbent body by performing embossing in a state where only the surface sheet 14 is folded and caused to adhere. However, in the top absorbent body, the absorbent body material 12*a* may exist also in the reinforced sections 25 and 26.

Furthermore, in the foregoing embodiments, an example was described in which the front end 20*a* side of the top absorbent body 20 is permanently joined at the reinforced section 26. However, the permanently joined section is not limited to the reinforced section 26 only, and may extend beyond the rear side end of the reinforced section 26 to a section of the top absorbent body 20 where the absorbent body material 12*a* exists.

Furthermore, in the foregoing embodiments, an example was described in which the hook member 22 for fixing the top absorbent body 20 in a state where the position of the top absorbent body 20 has been adjusted so as to closely contact with the bodily groove when the absorbent article 1 is worn is provided on the rear end side of the top absorbent body 20. However, a member such as the hook member 22 for fixing the top absorbent body does not necessarily have to be provided. In this case, by placing the top absorbent body in the bodily groove, the top absorbent body is sandwiched and held in the bodily groove. Moreover, in the foregoing embodiments, an example was described in which the rear end side of the top absorbent body is fixed to an undergarment with the hook member 22 in use. However, the hook member 22 may be disposed in a position in the center side in the longitudinal direction, that is, the hook member 22 may be disposed so as to oppose the base absorbent body 10 when the absorbent article 1 is worn, and the hook member 22 may be fixed to the base absorbent body 10.

Furthermore, in the foregoing embodiments, an absorbent article 1 was described in which the top absorbent body 20 is supplied together with the base absorbent body 10, the back face sheet 30, and the like. However, the top absorbent body 20 may be provided as, for example, an independent absorbent body and worn in a state in which the top absorbent body 20 is overlapped with a conventional sanitary napkin or the like that corresponds to the base absorbent body. In this case, the above-described top absorbent body 20 is supplied to the user in an independent state in which it is not joined to the base absorbent body 10, with an adhesive being applied to a side of the reinforced section 26, which is on the front end 20*a* side, that opposes a sanitary napkin and the applied adhesive is covered with a release sheet. The user disposes the independent top absorbent body 20 along the longitudinal direction of a separately prepared conventional sanitary napkin or the like, removes the release sheet, and adheres the front end 20*a* side of the independent top absorbent body 20 to the front end side of the sanitary napkin. Then, in the case where a rear end section of the adhered top absorbent body 20 is grasped by the user and the top absorbent body 20 is set along the bodily groove, the top absorbent body 20 is placed into the groove while being bent. At that time, since the bodily groove (the buttocks) is recessed, in the case where the top absorbent body 20 is pulled up, the top absorbent body 20 is protruded (mountain-folded) corresponding to the recess of the groove. Herein, as the method for joining the independent top absorbent body 20 to a sanitary napkin or the like, a male member of a mechanical fastener such as a hook member with a temporarily joined rear end side may be used as well as the adhesive described above. In this case, it is desirable that a female member of the mechanical fastener is provided on the side of the sanitary napkin to which the top absorbent body 20 is joined. However, in the case where the surface of the sanitary napkin is made of a nonwoven fabric such as an SMS nonwoven fabric, the independent top absorbent body 20 can be easily joined to the sanitary napkin as long as a male member of a mechanical fastener is provided on the front end side thereof.

Figure 18:
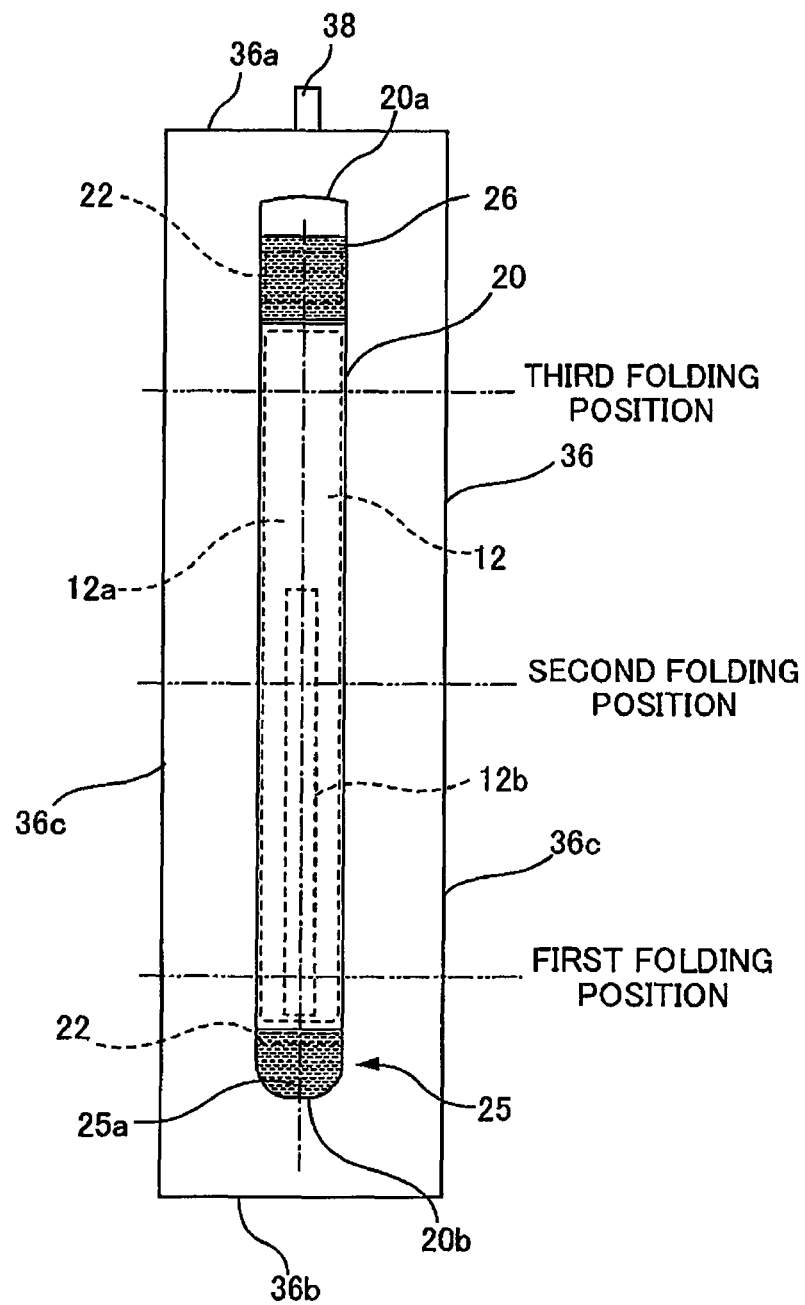
FIG. 18 is a view for illustrating a wrapping method of an independent top absorbent body.

In the case where the top absorbent body 20 is supplied as an independent absorbent body, for example, the top absorbent body 20 may be individually wrapped and supplied to the user. FIG. 18 is a view for illustrating a wrapping method of an independent top absorbent body.

As shown in FIG. 18, as is the case with the absorbent article 1 of the foregoing embodiments, the top absorbent body 20 is folded through three bending steps in which the top absorbent body 20 is bent at first to third folding positions and wrapped in the wrapping sheet 36.

More specifically, through the same steps as the steps through which the absorbent article 1 is folded as shown in FIG. 8, the top absorbent body 20 is folded by being bent toward the surface side so that the side of a face that is brought into contact with the body when worn is positioned on the inner side. Herein, the wrapping method will be described assuming that the absorbent article 1 in FIG. 8 is the independent top absorbent body 20.

The independent top absorbent body 20 is transported on the transporting table while being placed on the wrapping sheet 36. At the first folding position, the top absorbent body 20 and the wrapping sheet 36, which are transported, are folded at a side closer to the rear end than the first disk 60, by being bent upward at gradually increasing angles, while the top absorbent body 20 and the wrapping sheet 36 are transported sandwiched between the first disk 60 and the transporting table.

Subsequently, the top absorbent body 20 and the wrapping sheet 36 are transported to the position at which the second disk 62 is disposed in alignment with the second folding position. The top absorbent body 20 and the wrapping sheet 36 are folded at a side closer to the rear end than the second disk 62, by being bent upward at gradually increasing angles, while the top absorbent body 20 and the wrapping sheet 36 are transported sandwiched between the second disk 62 and the transporting table.

Furthermore, the top absorbent body 20 and the wrapping sheet 36 are transported to the position at which the third disk 64 is disposed in alignment with the third folding position. The top absorbent body 20 and the wrapping sheet 36 are folded at a side closer to the front end than the third disk 64, by being bent upward at gradually increasing angles, while the top absorbent body 20 and the wrapping sheet 36 are transported sandwiched between the third disk 64 and the transporting table.

In this manner, through the three bending steps, the top absorbent body 20 is singly folded and wrapped in the wrapping sheet 36. Then, the lead tape 38 provided on the side of the front end 36a of the wrapping sheet 36 is attached to the outer face of the wrapping sheet 36 on the side of the rear end 36b that has been already bent together with the top absorbent body 20. The wrapping sheet 36 that has been folded together with the top absorbent body 20 is sealed by causing edge sections 36c in the longitudinal direction to adhere, and the top absorbent body 20 that is contained in the wrapping sheet 36 in the form of a package is supplied to the user.

Thus, a plurality of independent top absorbent bodies 20 that have been individually wrapped may be further wrapped collectively and supplied to the user, or an individually wrapped top absorbent body 20 and an individually wrapped base absorbent body 10 to which the top absorbent body 20 can be joined may be further wrapped together and supplied to the user. Moreover, a plurality of top absorbent bodies 20 and a plurality of base absorbent bodies 10 to which the top absorbent bodies 20 can be joined may be wrapped in a single wrapping sheet and supplied to the user. In this case, the numbers of the top absorbent bodies 20 and the base absorbent bodies 10 wrapped in a single wrapping sheet do not have to be the same.

In addition to the above-described operations and effects, such an independent top absorbent body 20 has an advantage of being convenient to carry due to its size that is smaller than that of the absorbent article 1 in which the top absorbent body 20 and the base absorbent body 10 are made into a single body. That is to say, it is possible to handle menstrual blood according to the variations in the amount of menstrual blood by carrying the single top absorbent body 20 together with a conventional absorbent article, without carrying the absorbent article 1 or the like in which the top absorbent body 20 and the base absorbent body 10 are made into a single body in preparation for the case where the amount of menstrual blood or the like is large.

Further, the foregoing embodiments are merely for the purpose of facilitating understanding of the invention and are not to be interpreted as limiting the invention. The invention can of course be altered and improved without departing from the gist thereof, and equivalents are intended to be embraced therein.

The invention claimed is:

1. An absorbent article adapted to be worn by a wearer, said absorbent article comprising:
an absorbent article main body having a longitudinal direction, a width direction perpendicular thereto, and a thickness direction perpendicular thereto; and
an absorbent body overlapping the absorbent article main body along the longitudinal direction and including an absorbing member for absorbing fluid,
wherein
a first end section the absorbent body is undetachably joined to the absorbent article main body, and an opposite second end section of the absorbent body in the longitudinal direction is detachably joined to the absorbent article main body,
the absorbent body includes a first section on a wearer-facing side adapted to face the wearer in use and a second section on a non-wearer-facing side adapted to face away from the wearer in use,
the first section is elongatable more in the width direction than the second section of the absorbent body,
the absorbing member includes a thin-walled section extending along the longitudinal direction and in a center in the width direction of the absorbent body,
a thickness of the thin-walled section is less than that of the remaining section of the absorbent member,
the thin-walled section is closer to said first end section than to said second end section in the longitudinal direction,
the absorbent body is deformable to protrude toward the wearer when the absorbent article is worn, and
the thin-walled section is positioned on the wearer-facing side of the absorbent body.

2. An absorbent article adapted to be worn by a wearer, said absorbent article comprising:
an absorbent article main body having a longitudinal direction, a width direction perpendicular thereto, and a thickness direction perpendicular thereto; and
an absorbent body overlapping the absorbent article main body along the longitudinal direction and including an absorbing member for absorbing fluid,
wherein
first and second end sections of the absorbent body opposite each other in the longitudinal direction are each detachably joined to the absorbent article main body,
the absorbent body includes a first section on a wearer-facing side adapted to face the wearer in use and a second section on a non-wearer-facing side adapted to face away from the wearer in use,
the first section is elongatable more in the width direction than the second section of the absorbent body,
the absorbing member includes a thin-walled section extending along the longitudinal direction and in a center in the width direction of the absorbent body,
a thickness of the thin-walled section is less than that of the remaining section of the absorbent member,
the thin-walled section is closer to said first end section than to said second end section in the longitudinal direction,
the absorbent body is deformable to protrude toward the wearer when the absorbent article is worn, and
the thin-walled section is positioned on the wearer-facing side of the absorbent body.

3. An absorbent article according to claim 1, wherein
the absorbent body includes a sheet member for wrapping the absorbing member, and
the sheet member includes end sections which are overlapped and adhered to each other on the non-wearer-facing side of the absorbent body.

4. An absorbent article according to claim 3, wherein the sheet member comprises wrinkles adapted to be elongated in the width direction.

5. An absorbent article according to claim 1, wherein the absorbent body further comprises a leakage preventing sheet for preventing fluid from leaking, and the leakage preventing sheet includes a region which is, in the width direction, wider in a section on the non-wearer-facing side than in a corresponding section on the wearer-facing side.

6. An absorbent body adapted to be worn by a wearer and having a longitudinal direction, a width direction perpendicular thereto, and a thickness direction perpendicular thereto, said absorbent body comprising:
an absorbing member for absorbing fluid; and
a sheet member for wrapping the absorbing member, wherein
the absorbent body is adapted to overlap an absorbent article main body along the longitudinal direction,
the absorbent body includes a first end section of the absorbent body joinable to the absorbent article main body, and a second end section opposite to said first end section in the longitudinal direction and separable from the absorbent article main body,
the absorbent body includes a first section on a wearer-facing side adapted to face the wearer in use and a second section on a non-wearer-facing side adapted to face away from the wearer in use,
the first section is elongatable more in the width direction than the second section of the absorbent body,
the absorbing member includes a thin-walled section extending along the longitudinal direction and in a center in the width direction of the absorbent body,
a thickness of the thin-walled section is less than that of the remaining section of the absorbent member,
the thin-walled section is closer to said first end section than to said second end section in the longitudinal direction,
the absorbent body is deformable to protrude toward the wearer when the absorbent body is worn, and
the thin-walled section is positioned on the wearer-facing side of the absorbent body.

7. An absorbent body according to claim 6,
wherein the sheet member comprises end sections which are overlapped and adhered to each other on the non-wearer-facing side of the absorbent body.

8. An absorbent body according to claim 7, wherein the sheet member comprises wrinkles adapted to be elongated in the width direction.

9. An absorbent body according to claim 6,
wherein the absorbent body further comprises a leakage preventing sheet for preventing fluid from leaking, and
the leakage preventing sheet includes a region which is, in the width direction, wider in a section on the non-wearer-facing side than in a corresponding section on the wearer-facing side of the absorbent body.

10. An absorbent article according to claim 1, wherein
the absorbent body has a region adapted to contact a bodily fluid discharge opening of the wearer in use, and
an entirety of the thin-walled section extends rearward of said region and does not extend forward of said region.

11. An absorbent article according to claim 2, wherein
the absorbent body has a region adapted to contact a bodily fluid discharge opening of the wearer in use, and
an entirety of the thin-walled section extends rearward of said region and does not extend forward of said region.

12. An absorbent body according to claim 6, wherein
the absorbent body has a region adapted to contact a bodily fluid discharge opening of the wearer in use, and
an entirety of the thin-walled section extends rearward of said region and does not extend forward of said region.

13. An absorbent article according to claim 3, wherein the absorbent body further comprises a leakage preventing sheet directly bonded to the end sections of the sheet member for preventing fluid from leaking.

14. An absorbent article according to claim 3, wherein
the sheet member has a top section at the non-opposing side, and a bottom section at the non-wearer-facing side of the absorbent body and directly attached to the top section, and
the absorbent body further comprises a leakage preventing sheet directly bonded to the bottom section of the sheet member for preventing fluid from leaking.

15. An absorbent body according to claim 6, wherein the absorbent body further comprises a leakage preventing sheet for preventing fluid from leaking, said leakage preventing sheet being directly bonded to the sheet member at the non-wearer-facing side of the absorbent body.

16. An absorbent body according to claim 6, wherein the sheet member has a top section at the wearer-facing side, and a bottom section at the non-wearer-facing side and directly attached to the top section, and
the absorbent body further comprises a leakage preventing sheet directly bonded to the bottom section of the sheet member for preventing fluid from leaking.

17. An absorbent article according to claim 2, wherein
the absorbent body includes a sheet member for wrapping the absorbing member, and a leakage preventing sheet for preventing fluid from leaking, said leakage preventing sheet being directly bonded to the sheet member at the non-wearer-facing side of the absorbent body.

18. An absorbent article according to claim 2, wherein
the absorbent body includes a sheet member for wrapping the absorbing member, and a leakage preventing sheet for preventing fluid from leaking,
the sheet member has a top section at the wearer-facing side, and a bottom section at the non-wearer-facing side of the absorbent body and directly attached to the top section, and
the leakage preventing sheet is directly bonded to the bottom section of the sheet member.

* * * * *